(12) United States Patent
Dube et al.

(10) Patent No.: US 8,556,944 B2
(45) Date of Patent: Oct. 15, 2013

(54) SYSTEM AND METHOD FOR VERTEBRAL BODY PLATING

(75) Inventors: Michael A. Dube, Great Falls, MT (US); Frederick Marciano, Phoenix, AZ (US); Randall Porter, Phoenix, AZ (US); Nicholas Theodore, Phoenix, AZ (US); Eeric Truumees, Southfield, MI (US); Christopher McDonnell, Sandy Hook, CT (US); Daniel F. Justin, Logan, UT (US); Chad W. Lewis, Logan, UT (US)

(73) Assignee: Stryker Spine (FR)

( * ) Notice: Subject to any disclaimer, the term of this patent is extended or adjusted under 35 U.S.C. 154(b) by 853 days.

(21) Appl. No.: 11/888,330

(22) Filed: Jul. 31, 2007

(65) Prior Publication Data
US 2009/0036933 A1    Feb. 5, 2009

(51) Int. Cl.
*A61B 17/80*    (2006.01)

(52) U.S. Cl.
USPC ............ 606/282; 606/289; 606/290; 606/295

(58) Field of Classification Search
USPC ................................................. 606/280–299
See application file for complete search history.

(56) References Cited

U.S. PATENT DOCUMENTS

| | | | | |
|---|---|---|---|---|
| 2,401,856 | A * | 6/1946 | Brock | 411/517 |
| 5,904,683 | A * | 5/1999 | Pohndorf et al. | 606/287 |
| 6,235,033 | B1 * | 5/2001 | Brace et al. | 606/288 |
| 6,533,786 | B1 * | 3/2003 | Needham et al. | 606/282 |
| 7,001,389 | B1 | 2/2006 | Navarro et al. | |
| 7,766,948 | B1 * | 8/2010 | Leung | 606/305 |
| 8,114,139 | B2 * | 2/2012 | Sournac et al. | 606/286 |
| 2003/0199876 | A1 | 10/2003 | Brace et al. | |
| 2004/0068319 | A1 | 4/2004 | Cordaro | |
| 2004/0127896 | A1 * | 7/2004 | Lombardo et al. | 606/61 |
| 2004/0127897 | A1 * | 7/2004 | Freid et al. | 606/61 |
| 2004/0158246 | A1 * | 8/2004 | Assaker et al. | 606/61 |

(Continued)

FOREIGN PATENT DOCUMENTS

| | | |
|---|---|---|
| EP | 1764049 | 3/2007 |
| JP | 2003530196 A | 10/2003 |

(Continued)

OTHER PUBLICATIONS

Partial International Search Report, PCT/US2008/008986.

(Continued)

*Primary Examiner* — Michael T Schaper
(74) *Attorney, Agent, or Firm* — Lerner, David, Littenberg, Krumholz & Mentlik, LLP

(57) ABSTRACT

A spinal plating system for vertebral fixation includes a plate, a compression screw, multiple fixation members and polyaxially adjustable locking rings. The plate is shaped to conform to the curvature of the spine and the surfaces of the vertebral bodies. The compression screw fits through an insert, and together they are guided by the plate as the screw is driven into one of the vertebrae, producing compression between the adjacent vertebrae. A retaining lip on the plate prevents backout of the compression screw. The polyaxial locking rings can be polyaxially pivoted to attain a desired orientation, and are lockable to the plate to maintain the orientation. The fixation members fit through openings in the polyaxial locking rings and the plate to fix the plate to the vertebrae. Locking the polyaxial locking rings fixes the position of the fixation members relative to the plate, and prevents backout of the fixation members.

23 Claims, 30 Drawing Sheets

(56) References Cited

U.S. PATENT DOCUMENTS

| | | | |
|---|---|---|---|
| 2005/0033433 A1* | 2/2005 | Michelson | 623/17.11 |
| 2005/0049593 A1* | 3/2005 | Duong et al. | 606/69 |
| 2005/0137597 A1* | 6/2005 | Butler et al. | 606/69 |
| 2005/0182404 A1* | 8/2005 | Lauryssen et al. | 606/69 |
| 2005/0192580 A1* | 9/2005 | Dalton | 606/73 |
| 2005/0228386 A1* | 10/2005 | Ziolo et al. | 606/69 |
| 2005/0261690 A1 | 11/2005 | Binder et al. | |
| 2005/0277937 A1* | 12/2005 | Leung et al. | 606/69 |
| 2006/0036250 A1* | 2/2006 | Lange et al. | 606/69 |
| 2006/0089648 A1* | 4/2006 | Masini | 606/69 |
| 2008/0015592 A1 | 1/2008 | Long et al. | |

FOREIGN PATENT DOCUMENTS

| | | |
|---|---|---|
| JP | 2006521840 A | 9/2006 |
| JP | 2006524114 A | 10/2006 |
| JP | 2007083039 A | 4/2007 |
| JP | 2007152141 A | 6/2007 |
| JP | 2007515257 A | 6/2007 |
| JP | 2008012306 A | 1/2008 |
| WO | 2007009124 | 1/2007 |

OTHER PUBLICATIONS

International Search Report, PCT/US2008/008986.

* cited by examiner

SYSTEM AND METHOD FOR VERTEBRAL BODY PLATING

BACKGROUND OF THE INVENTION

The present invention generally relates to orthopedic medicine, and more particularly to systems and methods for spinal fixation.

Spinal plate systems are commonly used to fix adjacent vertebrae when treating spinal fractures or disorders, and for fusion of vertebrae.

In some instances it is desirable to create compression between adjacent vertebrae, to enhance the bone to graft apposition and provide for better fusion. Compression may be difficult to create and to maintain. If a bone screw feature is used to create the compression, backout of the bone screw can be a common problem, as the screw may work its way backwards out of the bone. Backout prevention features have been designed which are complicated mechanisms with multiple parts. It would be desirable to have a compression screw retention feature which is a monolithic part of the bone plate.

Another important aspect of bone plating systems is the orientation of the fixation members which fix the spinal plate to the vertebrae. Fixation members should pass through hard cortical bone to firmly fix the plate to the vertebrae. Additionally, the fixation members must avoid nervous and vascular structures enclosed by and adjacent to the vertebrae. Each fixation member may require a separate orientation which must be permanently fixable. Therefore, it is desirable to provide a system to individually guide the fixation members and lock their orientations relative to the vertebrae.

The shape and curvature of a spinal plate is significant feature of its design. A plate with a straight or flat bone apposition surface may be difficult to fix to the vertebral surface, as gaps may be present between the surface of the vertebral bodies and the plate. There is need for a plate which is not only curved to match the lordotic curve of the spine, but also has a bone apposition side shaped to conform to the surfaces of the vertebrae.

SUMMARY OF THE INVENTION

A spinal plating system for fixation of adjacent vertebrae includes a plate, a compression member, and multiple fixation members. The compression member comprises a compression screw which fits through an insert which is monolithically formed with the plate, and together they are guided by the plate as the screw is driven into through an aperture in the plate into one of the vertebrae, producing compression between the adjacent vertebrae. The fixation members attach the plate to the vertebrae.

In another embodiment, a spinal compression implant of the present invention includes a plate adapted to attached to a first vertebra. The implant also includes a slot formed in the plate, the slot having a ramp and a monolithic lip extending over one end of the ramp. A screw is inserted in the slot and threaded in a second vertebra. When the second screw is tightened, the second screw moves along the ramp and under the lip and compresses together the second vertebra and the first vertebra. The implant also includes at least one fixation hole formed in the plate. A fixation screw is inserted in the fixation hole and threaded in the first vertebra to attach the plate to the first vertebra.

In yet another embodiment, the implant includes a plate having a bone apposition side and configured to be attached to a first vertebra and a second vertebra. The bone apposition side of the plate has a longitudinal axis and a transverse axis, and the plate is bent about the transverse axis and curved about the longitudinal axis. The plate also has an elongated ridge extending normal to the bone apposition side.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for fixation of spinal vertebrae. Those of skill in the art will recognize that the following description is merely illustrative of the principles of the invention, which may be applied in various ways to provide many different alternative embodiments.

Figure 1:
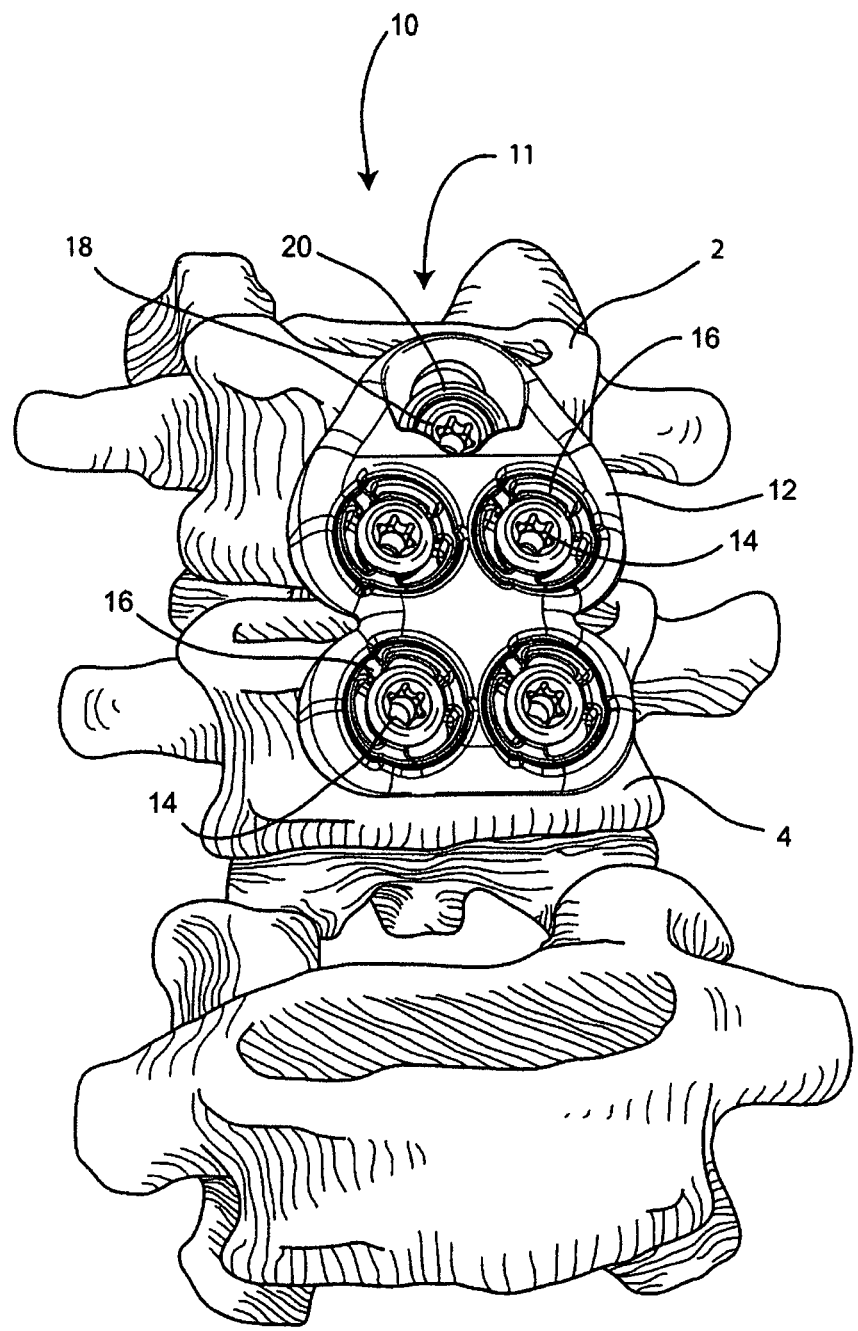
FIG. 1 is a perspective view of a lumbar plate system affixed anteriorly to a portion of the spine, including a lumbar plate with polyaxial locking rings and a compression insert, a compression screw, and fixation members.

Referring to FIG. 1, a lumbar plate system 10 is shown attached to the anterior side of a first vertebra 2 and a second vertebra 4. The lumbar plate system 10 comprises a plate assembly 11, a plurality of fixation members 14, and a compression screw 18 with a compression insert 20. The plate assembly 11 comprises a lumbar plate 12 and a plurality of polyaxial locking rings 16. For the purposes of this invention, a compression screw is a device that functions to create and maintain compressive force between vertebrae. The term compression screw does not refer to a unique configuration or shape of the screw but only the function of the screw. Bone screws already known to the art may be used as compression screws in this invention when fitted with a surrounding insert.

Figure 2:
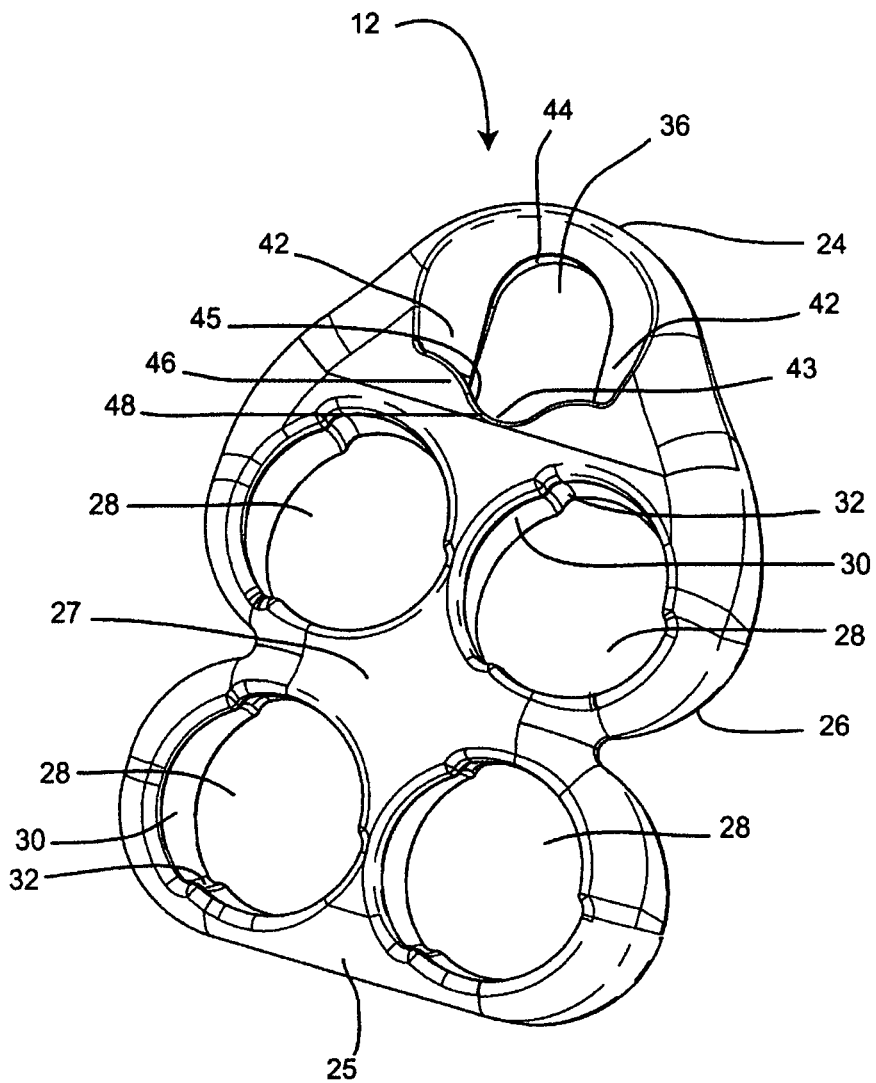
FIG. 2 is a perspective view of the lumbar plate of FIG. 1.

Referring to FIG. 2, the lumbar plate 12 is displayed in a perspective view. The plate assembly 11 is manufactured so that the polyaxial locking rings 16 are inseparable from the plate 12, the locking rings 16 retained within the fixation member holes 28. However, for clarity in the viewing the lumbar plate 12, the polyaxial locking rings 16 are absent from FIG. 2.

The lumbar plate 12 is of a generally flat hourglass shape, with a wide, slightly elongated first end 24 and a similarly wide second end 25. When affixed anteriorly on the spine as in FIG. 1, the lumbar plate 12 may be oriented with either the first end 24 in the cephalic direction or the second end 25 in the cephalic direction. The lumbar plate 12 also has a bone apposition side 26 and an outer-facing side 27.

Two fixation member holes 28 perforate the first end 24, and two more perforate the second end 25. In this embodiment of the invention, four fixation member holes 28 are shown in the plate. However, in other embodiments, the number and arrangement of fixation member holes 28 may vary. The fixation member holes 28 are located so that, when added, the fixation members 14 are driven into the harder bone cortex at the edges of the vertebrae, as opposed to the softer cortex near the centers of the vertebrae. Each fixation member hole 28 is generally circular and is encircled by a wall 30. At three equally spaced points along each wall 30 is an indentation 32, where the wall 30 is recessed slightly into the surrounding lumbar plate 12 material.

Perforating the lumbar plate 12 between the first end 24 and the fixation member holes 28 is a compression aperture 36. The compression aperture 36 has a generally oval, elongated shape with a first end 44 and a second end 45. Each lateral side of the compression aperture 36 is a ramp 42, which rise from the aperture 36 at the second end 45, widen out on each lateral side, and join at the first end 44, forming a smooth curve around the aperture 36. At the second end 45 of the aperture 36 is a retaining wall 43 which terminates in an overhanging lip 46. A semicircular notch 48 is cut into the lip 46, centered over the compression aperture 36. The compression aperture 36, retaining wall 43 and lip 46 are monolithically formed parts of the lumbar plate 12.

Figure 3:
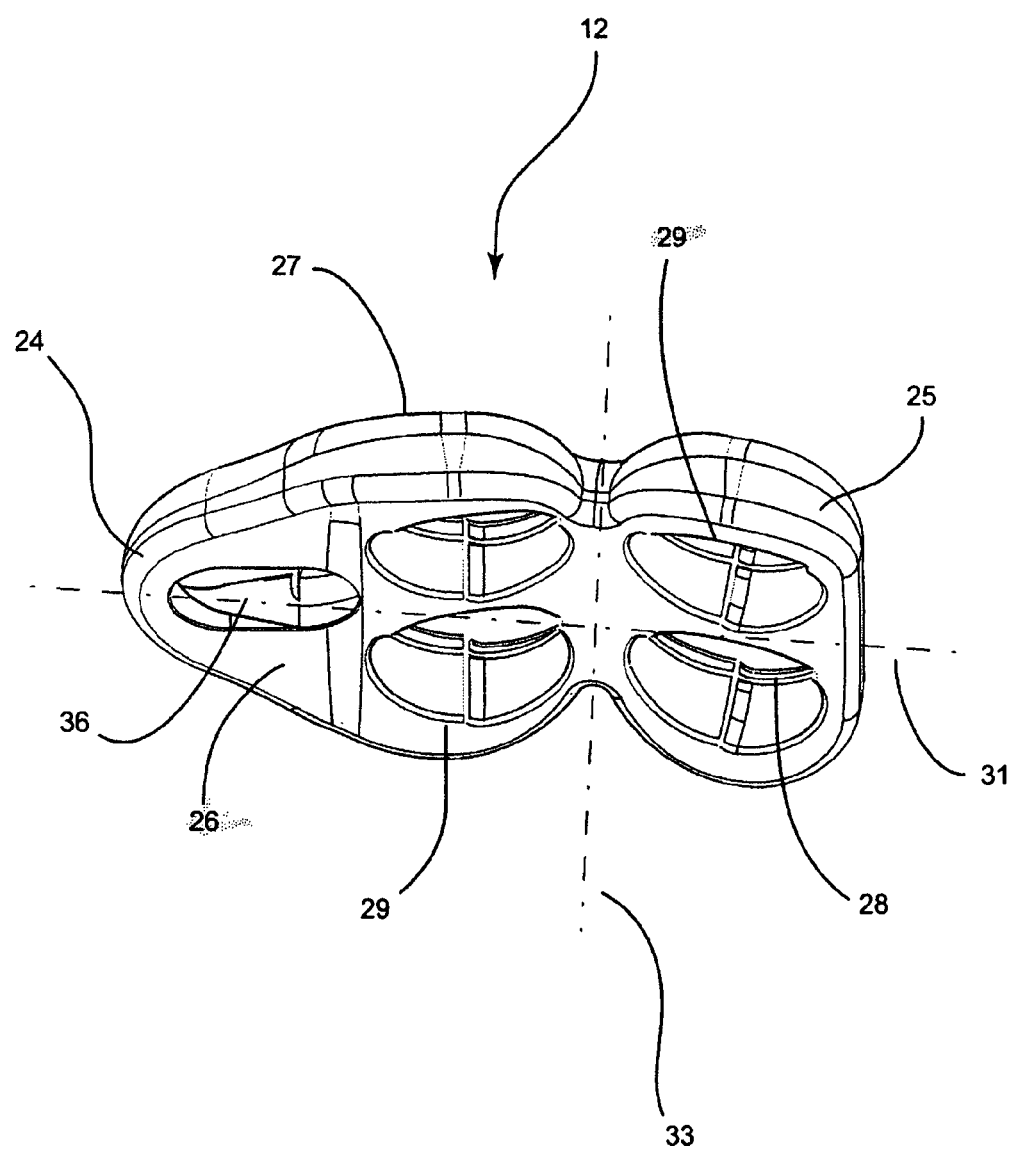
FIG. 3 is a perspective view of a bone apposition side of the lumbar plate of FIG. 1.

Referring to FIG. 3, a lateral perspective view shows the bone apposition side 26 of the plate 12. The bone apposition side 26 has longitudinal axis 31 and a transverse axis 33. The plate 12 is concavely curved about the longitudinal axis 31, such that the curved bone apposition side 26 forms a continuously curving radius about the longitudinal axis 31. The plate 12 is simultaneously bent about the transverse axis 33, the bend forming an angle between the two ends 24, 25. Additionally, the plate has an outwardly projecting elongated ridge 29 normal to the bone apposition side 26 on each end 24, 25. The ridges 29 are multiple adjacent convex curves on the transverse axis 33 at each end 24, 25, and allow the plate 12 to fit to the anatomical peripheral surfaces of the vertebral bodies when placed against the vertebrae.

Figure 4:
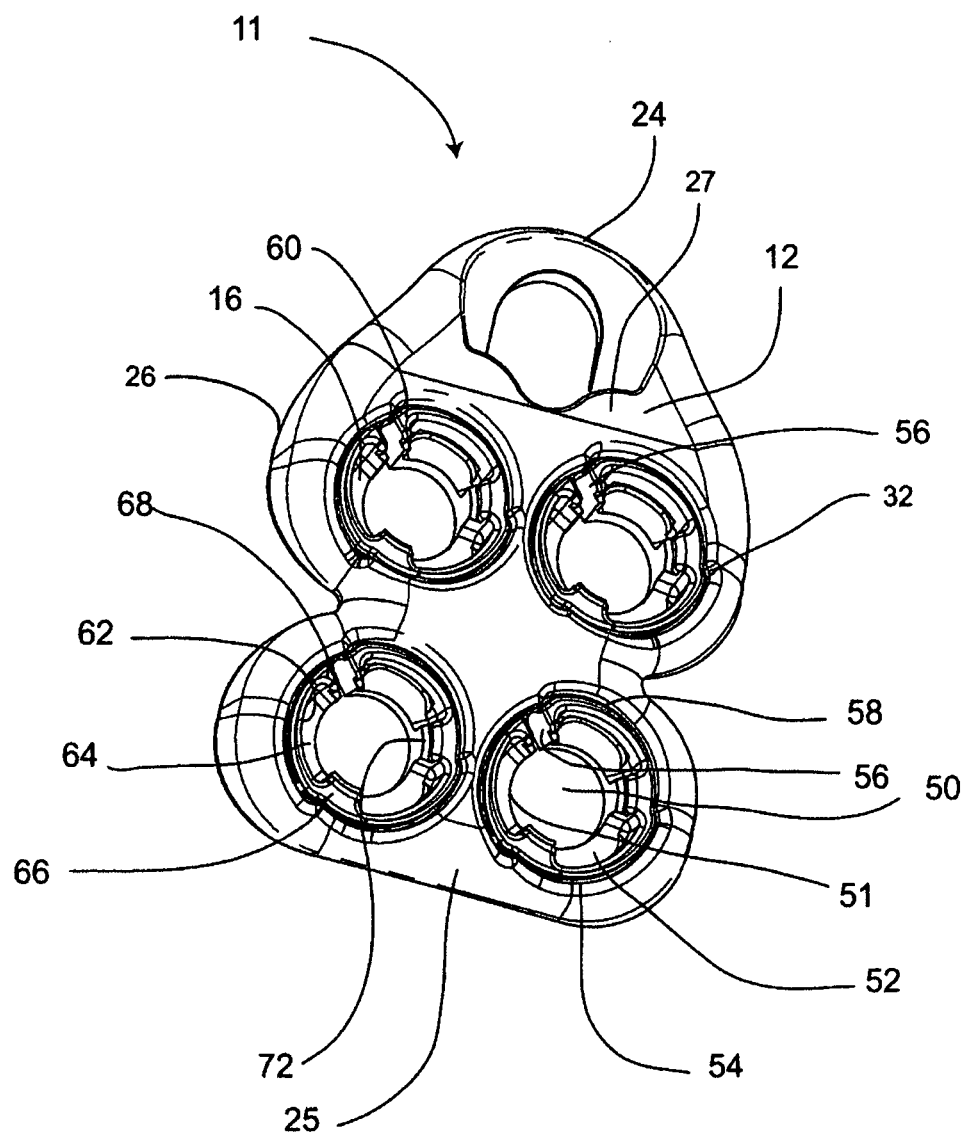
FIG. 4 is a perspective view of a lumbar plate assembly, including a lumbar plate and polyaxial locking rings.
Figure 4A:
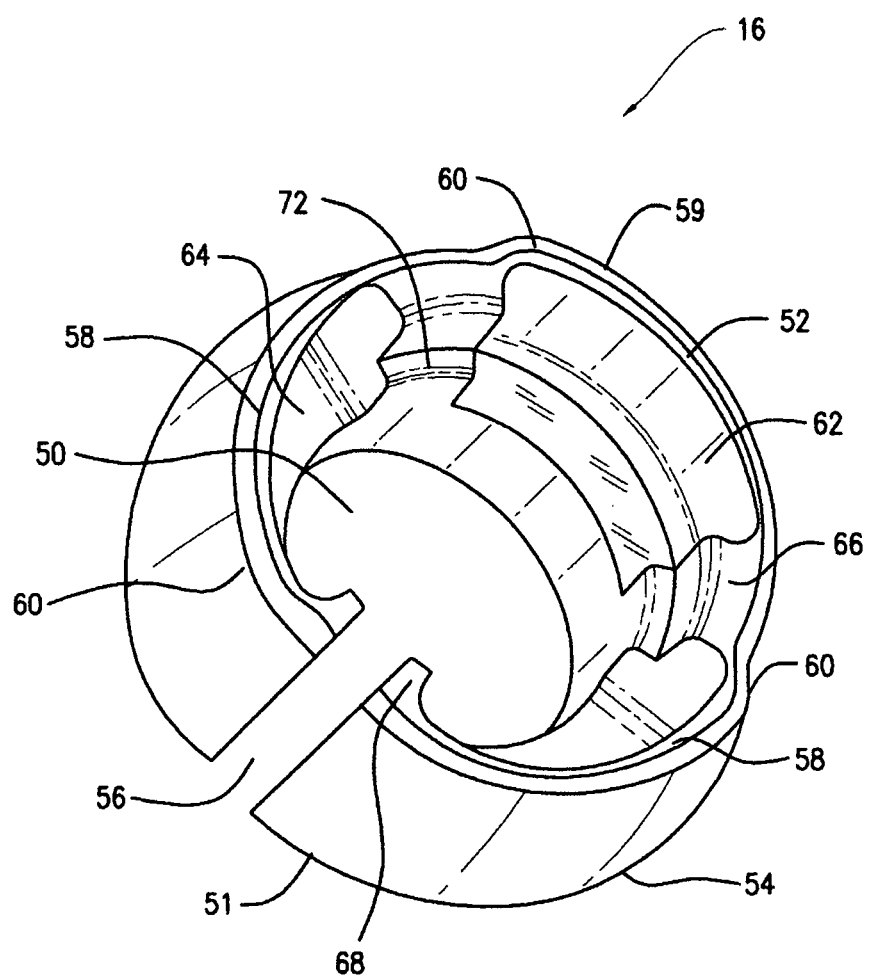
FIG. 4A is a perspective view of the polyaxial locking ring of FIG. 4.

Referring to FIG. 4, an enlarged perspective view shows the plate assembly 11. The polyaxial locking rings 16 are integral parts of the plate assembly 11 and are not removable from the fixation member holes 28. Each polyaxial locking ring 16 (FIG. 4A) is of a trilobial circular shape with a central bore 50. The ring 16 has two sides, a flat side 51 which aligns with the bone apposition side 26, and a notched locking side 52 which is visible on the outer facing side 27. The outer circular surface of the polyaxial locking ring 16 is an outer ring wall 54. The outer ring wall 54 is a trilobial, discontinuous circle, broken by a gap 56. The outer ring wall 54 is generally smooth, and is divided into three equally sized lobes 58 by three projections 60. Each projection 60 is a outward swelling of the ring wall 54, and is configured to fit into an indentation 32 in the fixation member hole wall 30.

The inner circular surface of the polyaxial locking ring 16 is an inner ring wall 62. The inner ring wall 62 is not smooth but uneven, comprised of three pockets 64 alternating with two ribs 66, which form dividers between the pockets. The third division between the pockets 64 is a split rib 68, which is split by the presence of the gap 56. Each rib 66 and the split rib 68 has a step 72 located partway down the length of the rib, shaped to hold the edge of a fixation member 14. The polyaxial locking ring 16 is flexibly expandable so that when the inner ring wall 62 is pushed outward, the projections 60 fit into the indentations 32 in the wall 30, the gap 56 widens and the diameter of the ring 16 increases. This expansion allows space for insertion of tools for preparation of the fixation members 14 prior to their placement through the locking rings 16.

The polyaxial locking rings 16 are also lockable to the plate 12, by rotation of the polyaxial locking ring 16. When the polyaxial locking ring 16 is rotated with a torque wrench the projections 60 on the outer ring wall 54 are forced past the indentations 32 in the fixation member hole wall 30. Once the ring 16 is thus torqued, residual compression and the outward spring bias of the ring 16 keep it locked in place.

Figure 5:
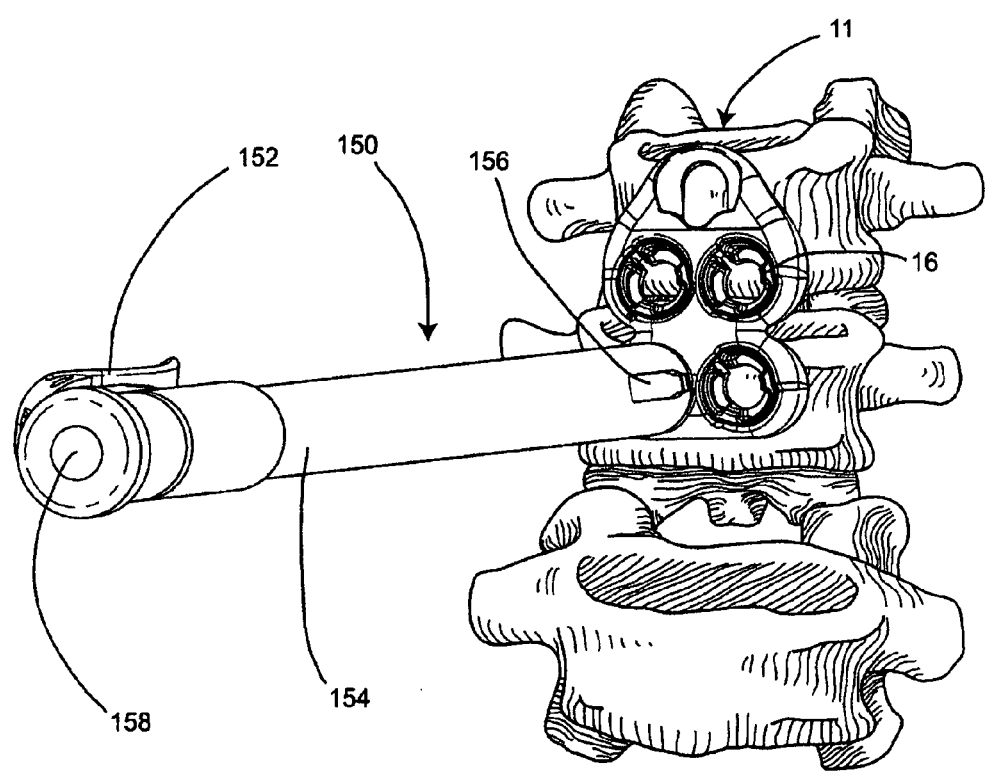
FIG. 5 is perspective view of the lumbar plate assembly of FIG. 4, with a locking guide secured to one polyaxial locking ring.

Referring to FIG. 5, the plate assembly of FIG. 4 is shown, held against a portion of the spine by a locking guide 150. The locking guide 150 is configured to fit into any of the polyaxial locking rings 16. The locking guide 150 is lockable to any polyaxial locking ring 16 and can polyaxially pivot, individually, each polyaxial locking ring 16 until the desired orientation for the particular fixation member 14 is found. This movement enables the surgical personnel to orient and place each fixation member 14 in a precise orientation to the vertebra, avoiding nervous and vascular structures. Then the locking guide 150 is locked in place, holding that orientation, while the fixation member 14 is prepared and driven. The locking guide 150 has a lever 152, a shaft 154, a locking mechanism 156 and a tool bore 158.

Figure 6:
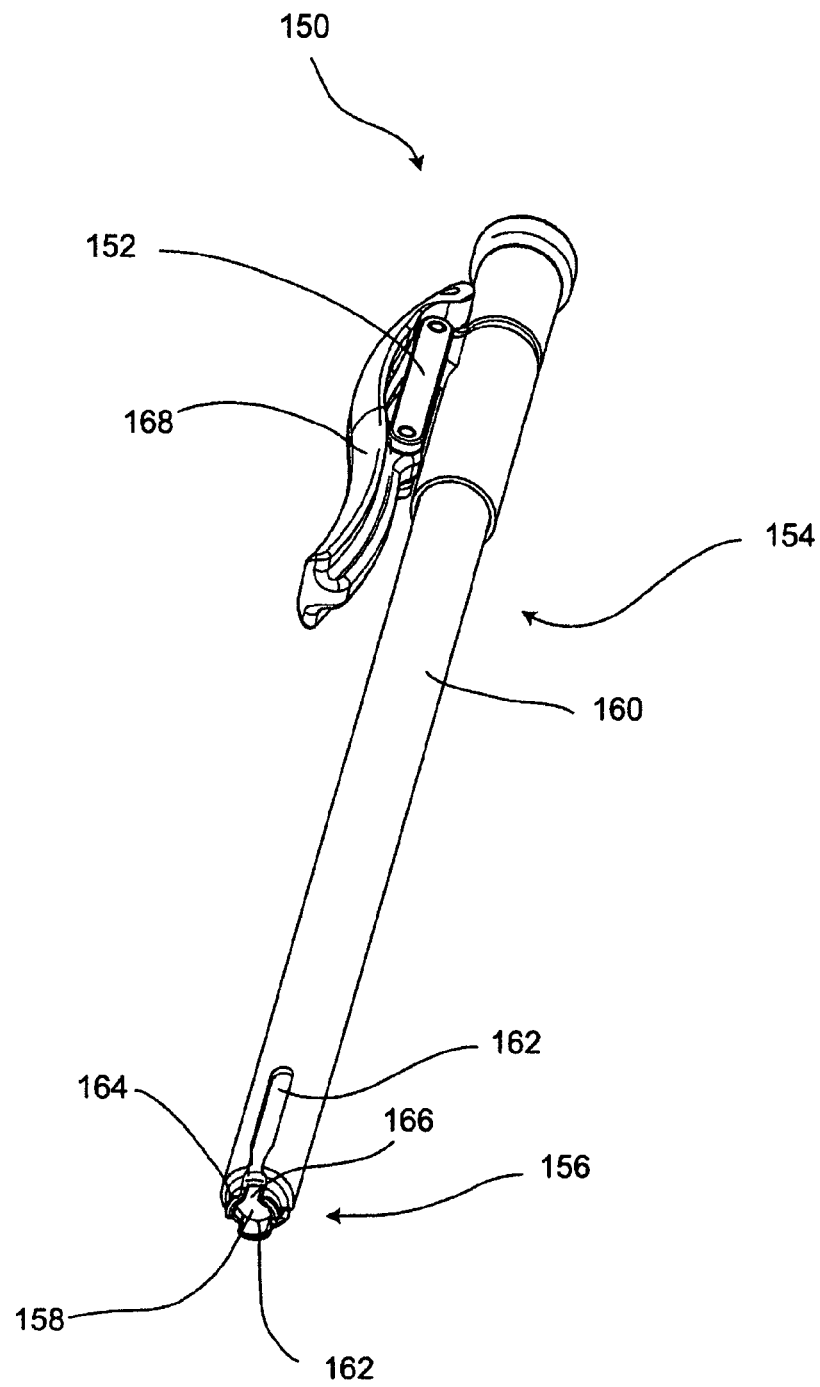
FIG. 6 is a perspective view of the locking guide of FIG. 5.

FIG. 6 displays the locking guide 150 in greater detail. The shaft 154 comprises a outer hollow sleeve 160 and an inner expander 162. The locking mechanism 156 is at the distal end of the hollow sleeve 160, and comprises three prongs 164 alternating with three slots 166. Connected to the proximal end of the hollow sleeve 160 is a linkage 168, which is also connected to the lever 152. In turn, the lever 152 is also connected to the proximal end of the expander 162. When the lever 152 is lifted, the expander 162 is lifted within the hollow sleeve 160. When the lever 152 is lowered, the expander 162 slides distally within the hollow sleeve 160. As the distal end of the expander 162 reaches the prongs 164, it contacts the prongs 164, pushing them outward and widening the slots 166.

The locking guide 150 connects to and holds a polyaxial locking ring 16 open so that a stabilization pin 120 or a fixation member 14 can be oriented and driven into a vertebra. The prongs 164 are configured to fit in the pockets 64 of a polyaxial locking ring 16, while the slots 166 fit around the ribs 66, 68. The locking guide 150 and the polyaxial locking ring 16 are polyaxially pivoted together until the desired orientation to the vertebra is found. The lever 152 is lowered and the prongs 164 are expanded outward by the expander 162, forcing the polyaxial locking ring 16 to expand in diameter. The spring bias of the ring causes it to hold to the prongs 164. The locking guide 150 and the polyaxial locking ring 16 remain locked in that orientation while a stabilization pin 120 and/or a fixation member 14 are inserted, then the lever 152 is raised and the locking guide 150 is disengaged from the polyaxial locking ring 16.

Figure 7:
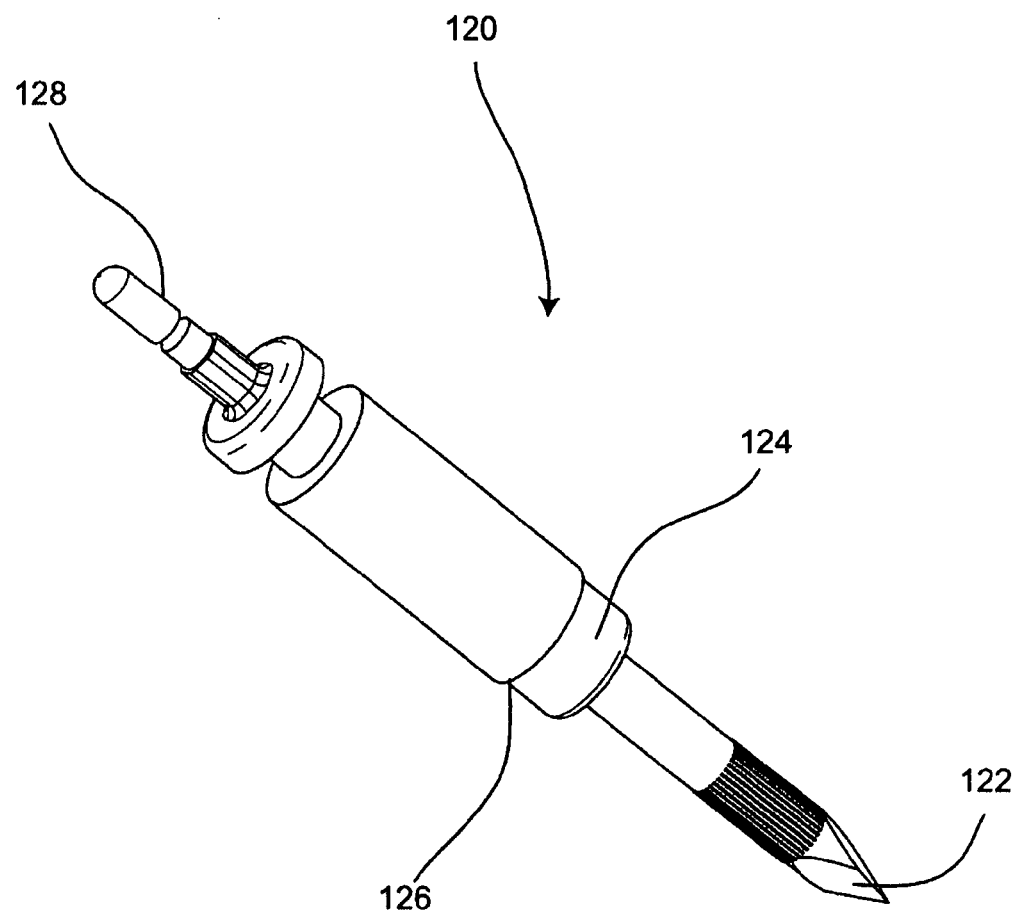
FIG. 7 is a side perspective view of a stabilization pin.

FIG. 7 displays a stabilization pin 120 in greater detail. The pin 120 has a narrow point 122 at the end of a shaft 124. Near the midpoint on the shaft 124, it is encircled by a flange 126. A head 128 is located at the opposite end of the shaft 124 from the point 122. The stabilization pin 120 is inserted through one of the polyaxial locking rings 16 into one of the vertebra to temporarily hold the plate 12 in place on the spine while the fixation members 14 are driven.

Figure 8:
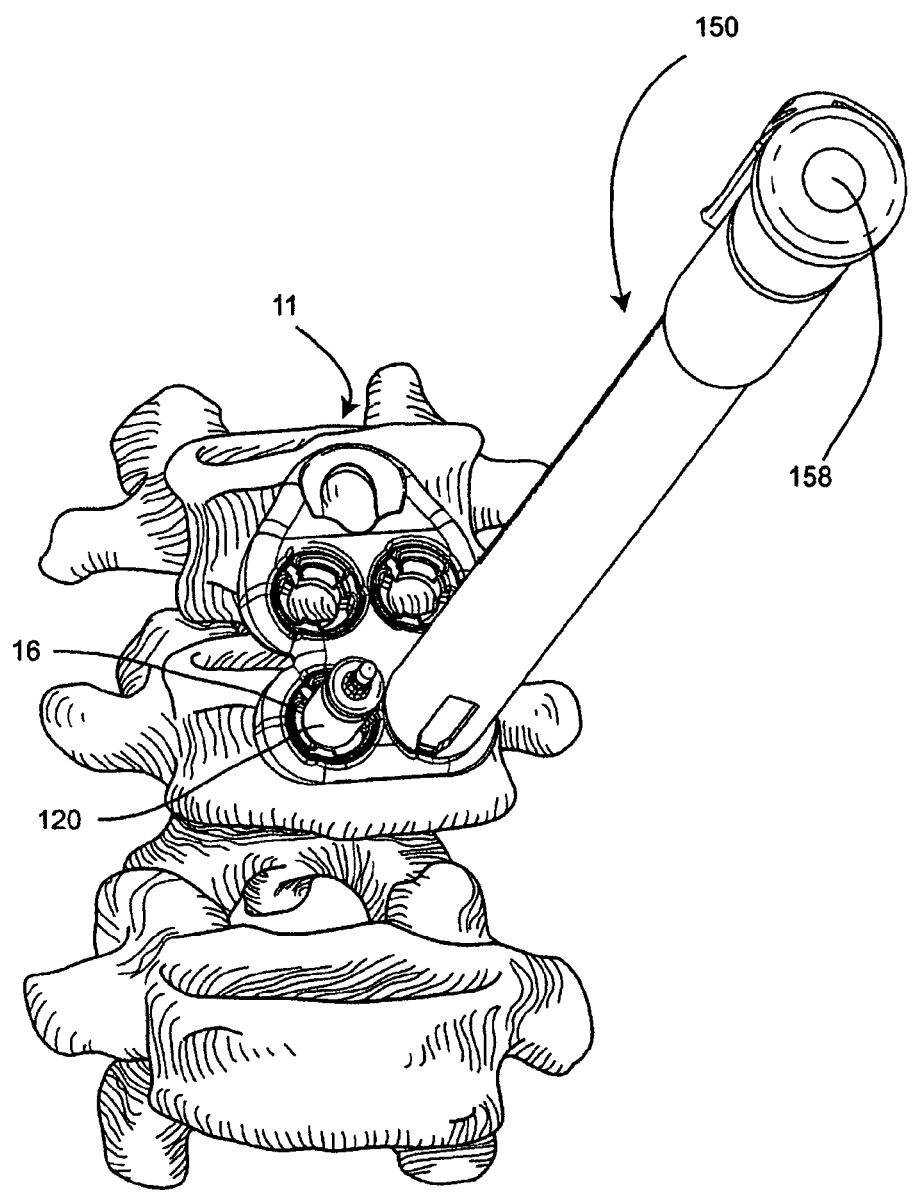
FIG. 8 is a perspective view of the lumbar plate assembly of FIG. 4, with a stabilization pin inserted and a locking guide secured to one polyaxial locking ring.

Referring to FIG. 8, a plate assembly 11 and locking guide 150 are shown, with the addition of a stabilization pin 120 in one of the polyaxial locking rings 16. A pin inserter 130 (not shown) is used to drive the pin in place. The pin 120 is placed on the end of the pin inserter 130, and together they are slid into the tool bore 158 of the locking guide 150. The inserter 130 drives the pin 120 through the polyaxial locking ring so that the point 122 and a portion of the shaft 124 pass through the bore 50, stopping when the flange 126 contacts the steps 72 on the ribs 66, 68. The pin inserter 130 is withdrawn from the locking guide 150. The locking guide is unlocked from the polyaxial locking ring 16, and locked to the adjacent polyaxial locking ring 16 to prepare to drive a fixation member 14.

When driven through a polyaxial locking ring 16, the pin 120 may be optionally locked in place by rotating the polyaxial locking ring 16 with a torque wrench (not shown). When the polyaxial locking ring 16 is rotated with the torque wrench, the projections 60 on the outer ring wall 54 are forced past the indentations 32 in the fixation member hole wall 30. Once the ring 16 is thus torqued, residual compression and the outward spring bias of the ring 16 keep it locked in place to the plate 12. Simultaneously, as the ring 16 is torqued, the inner ring wall 62 closes around the shaft 124, clamping the stabilization pin 120 in place.

Figure 9:
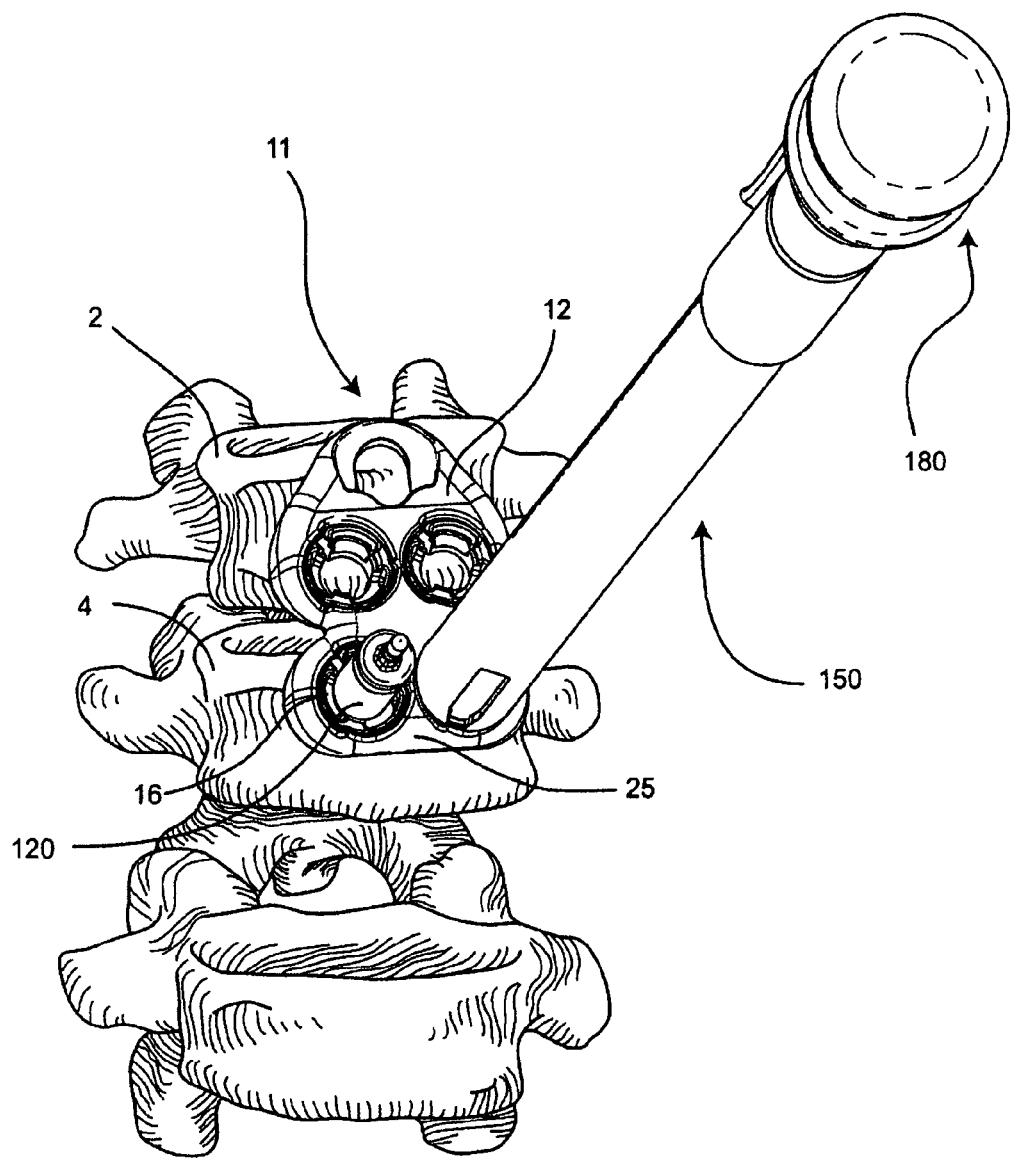
FIG. 9 is a perspective view of the lumbar plate assembly of FIG. 8, with an awl inserted in the locking guide.

FIG. 9 is a perspective view of the locking guide 150 locked in place on the plate assembly 11, in preparation for adding the first fixation member 14. The first fixation member 14 will be added to one fixation member hole 28/polyaxial locking ring 16 pair in the second end 25 of the lumbar plate 12. This is so the first fixation member 14 will be driven into the vertebra 4 adjacent to the vertebra 2 into which the compression screw 18 will be driven. An awl 180 is shown inserted in the tool bore 158.

Figure 10:
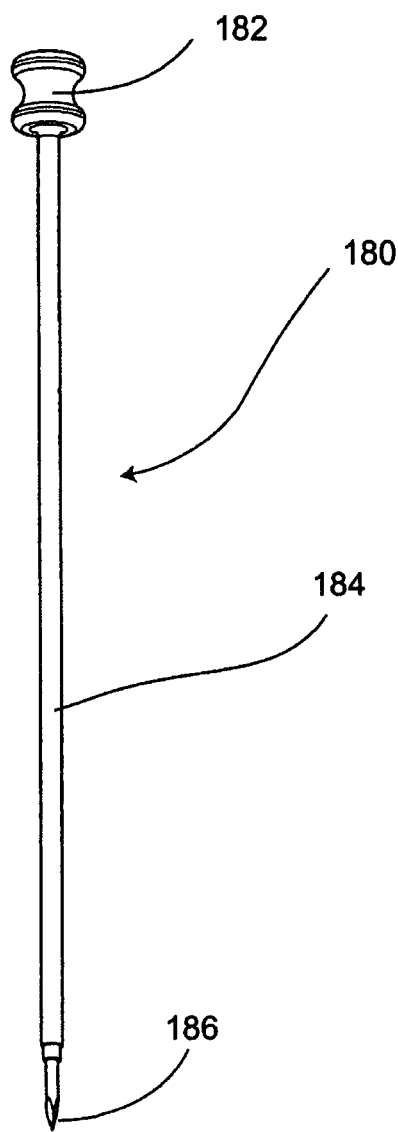
FIG. 10 is a side view of the awl of FIG. 9.

FIG. 10 displays the awl 180 in greater detail. The awl 180 has a handle 182, a shaft 184 and a sharp tip 186. The awl is inserted in the tool bore 158 and the sharp tip 186 is used to break through the hard cortical bone at the surface of the vertebra. The awl 180 is inserted until the tip 186 passes through the hard cortical bone on the first side of the vertebra, through the softer cancellous bone, and reaches the hard cortical bone on the opposite side. The handle 182 at the proximal end of the shaft prevents the awl from reaching too far into the bone. The handle 182 is too wide to fit into the tool bore 158, so the awl 180 will stop when the handle 182 contacts the proximal end of the tool bore 158. Once the hole in the vertebra is created, the awl 180 is removed from the tool bore 158. Alternatively, a drill (not shown) may be used to drill through the hard cortical bone.

Figure 11:
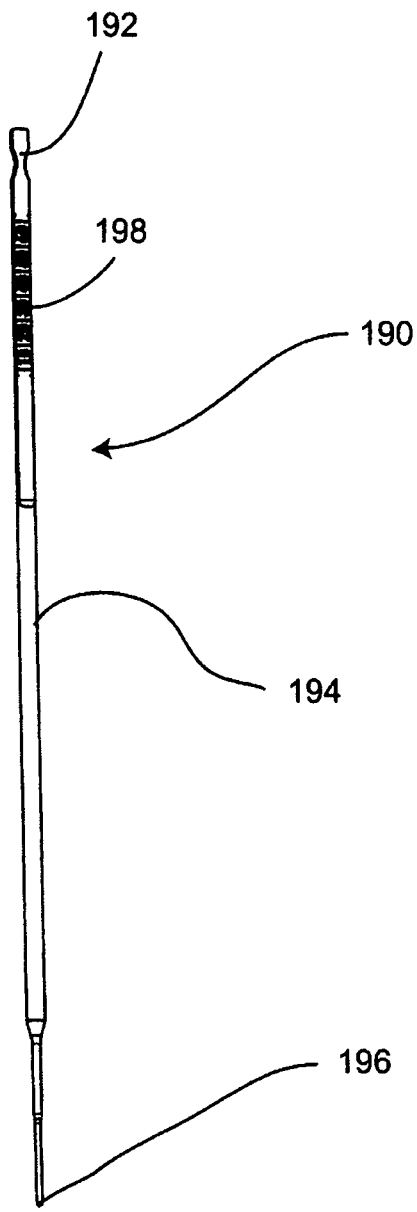
FIG. 11 is a side view of a depth gauge.

Referring to FIG. 11, a depth gauge 190 is used to measure the depth of the hole created by the awl 180. The depth gauge 190 has a proximal end 192, a shaft 194, a distal end 196, and depth markings 198. The distal end 196 of the depth gauge 190 is inserted into the tool bore 158, in the same manner as the awl 180. When the distal end 196 reaches the hard cortical bone on the far side of the cancellous bone, the depth marking 198 on the side of the shaft 194 is read and recorded, and the depth gauge 190 is removed. The depth marking 198 is used to choose the correct length fixation member 14.

Figure 12:
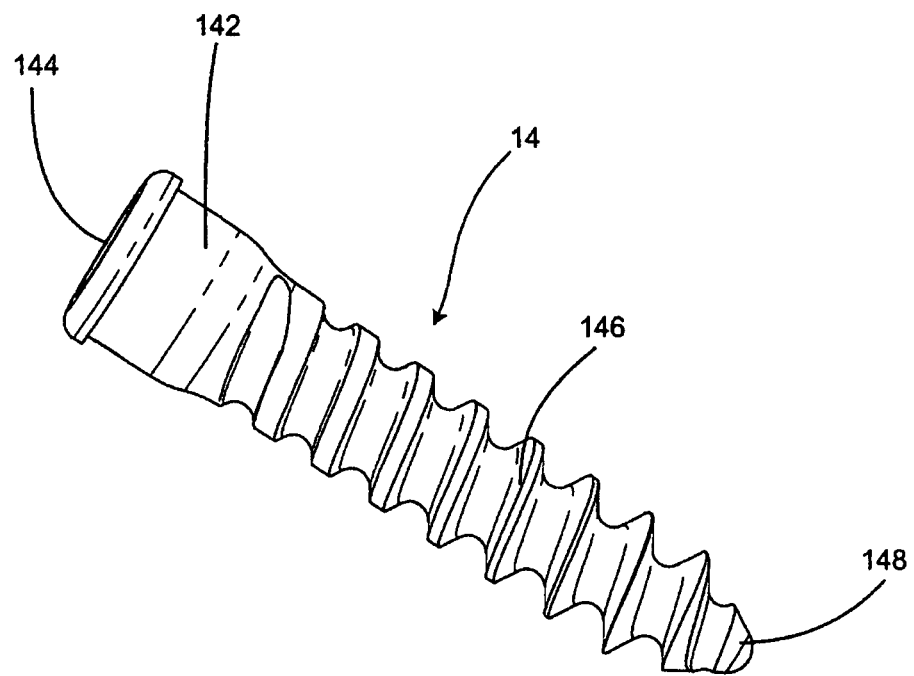
FIG. 12 is an enlarged perspective side view of a fixation member of FIG. 1.

FIG. 12 displays the fixation member 14. The fixation member 14 has an elongated head 142 with a torx slot 144. The head 142 extends to a threaded portion 146, which terminates at a tip 148. The threaded portion 146 has cancellous thread near the head 142, and transitions to cortical thread near the tip 148. In this embodiment of the invention, the slot 144 is of a torx shape; in other embodiments the slot 144 could be a straight slot, a Phillips slot, or of slot of another shape. The fixation members 14 can be of various lengths and diameters, to fit the particular size of the plate assembly 11 and the vertebrae.

Figure 13:
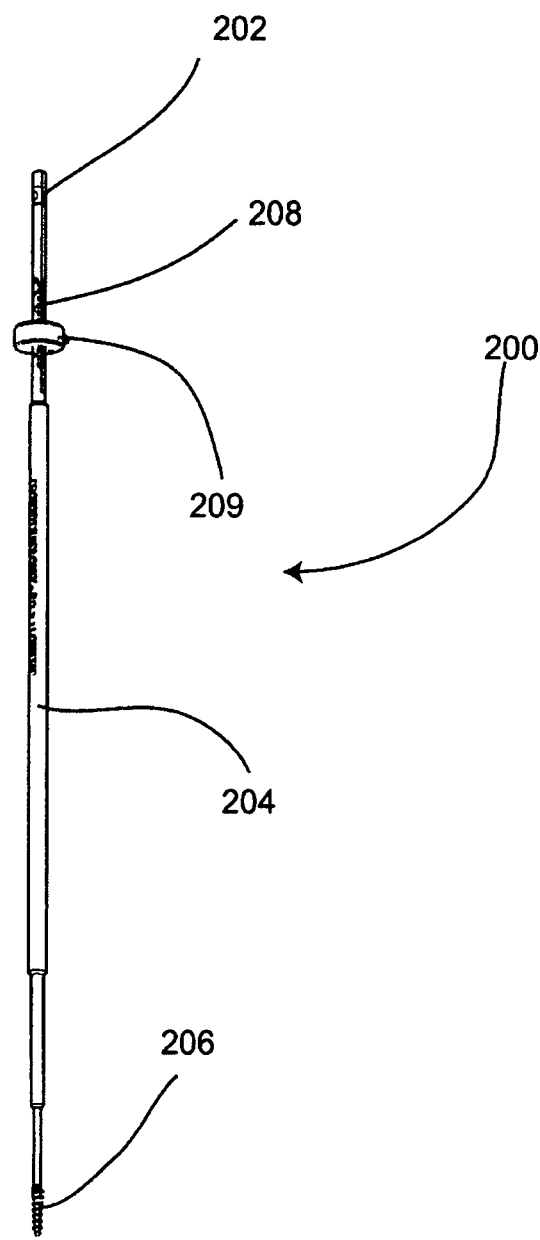
FIG. 13 is a side view of a tap.

Referring to FIG. 13, a tap 200 is used to tap the hole in the vertebra. The tap 200 has a proximal end 202, a shaft 204, and a tap bit 206. On the side of the shaft 204 are depth markings 208 which are in the same scale as the depth markings 198 on the depth gauge 190. A stop disk 209 encircles the shaft 204 at the level of the depth markings 208. Outside of the locking guide 150, the tap 200 is lined up parallel to the depth gauge 190, and the depth marking 208 on the tap 200 which matches the depth marking 198 on the depth gauge 190 is located. The stop disk 209 on the tap 200 is locked at that same depth marking 208. The tap 200 is inserted in the tool bore 158 and turned, tapping a threaded hole in the vertebra for the fixation member 14. The tap bit 206 of the tap 200 is long enough so that both the near cortical bone and the far cortical bone in the vertebra are tapped. When the stop disk 209 contacts the proximal end of the tool bore 158, the tap 200 cannot go any farther and the correct length hole has been tapped. The tap 200 is removed from the tool bore 158.

Figure 14:
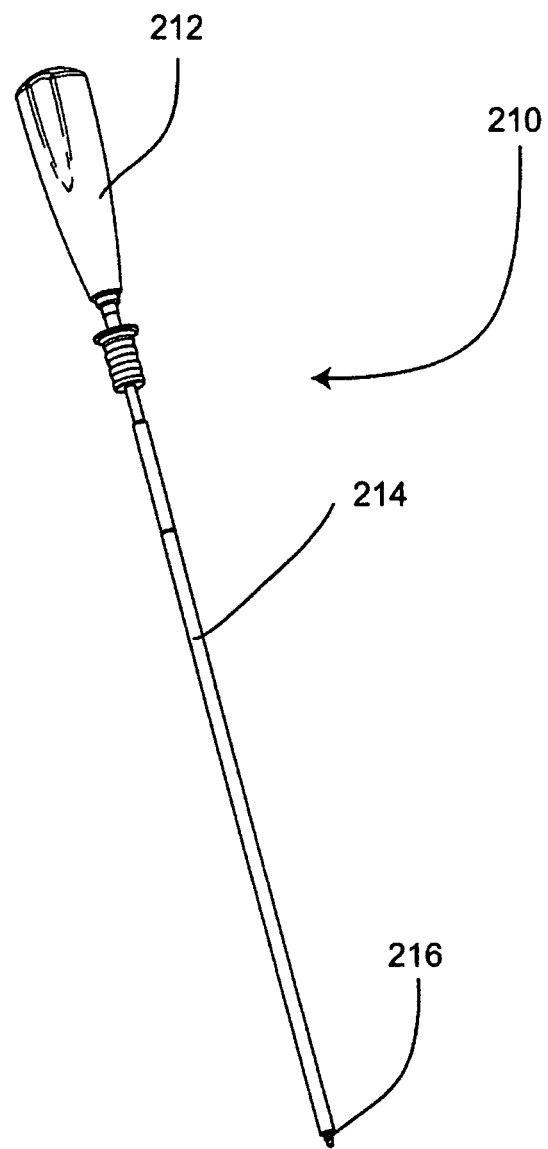
FIG. 14 is a side view of a screwdriver.

Referring to FIG. 14, a screwdriver 210 is shown. The screwdriver 210 has a handle 212, a shaft 214, and a torx driver tip 216. A fixation member 14 is placed on the torx driver tip 216, and fixation member 14, driver tip 216 and shaft 214 are inserted in the tool bore 158. The handle 212 is turned to drive the fixation member 14 into the vertebra. The fixation member 14 is driven through both the near cortical and far cortical bone of the vertebral body, accomplishing bi-cortical fixation. Once the fixation member 14 is driven into the full length of the tapped hole in the bone, the final turns of the screwdriver 210 lag the fixation member 14, drawing the lumbar plate 12 against the vertebra. The screwdriver 210 is removed from the tool bore 158, and the locking guide 150 is unlocked by raising the lever 152, and removed from the polyaxial locking ring 16.

Figure 15:
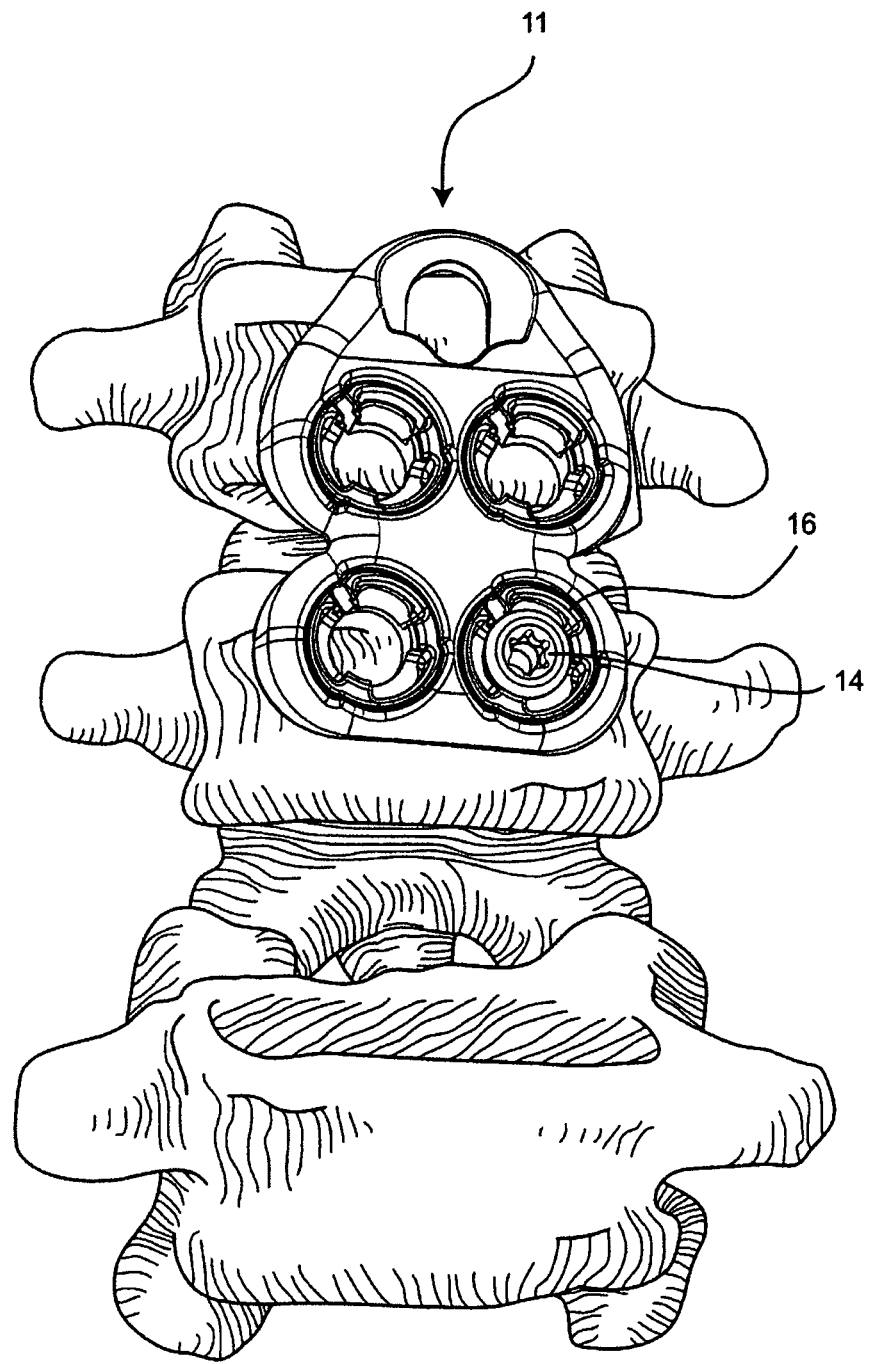
FIG. 15 is a perspective view of the lumbar plate assembly of FIG. 8, with a fixation member affixed therethrough.

Referring to FIG. 15, a plate assembly 11 is shown affixed to the spine with one fixation member 14. The stabilization pin 120 has been removed to prepare for placement of the second fixation member 14. The stabilization pin 120 can be removed by the insertion tool 130.

Figure 16:
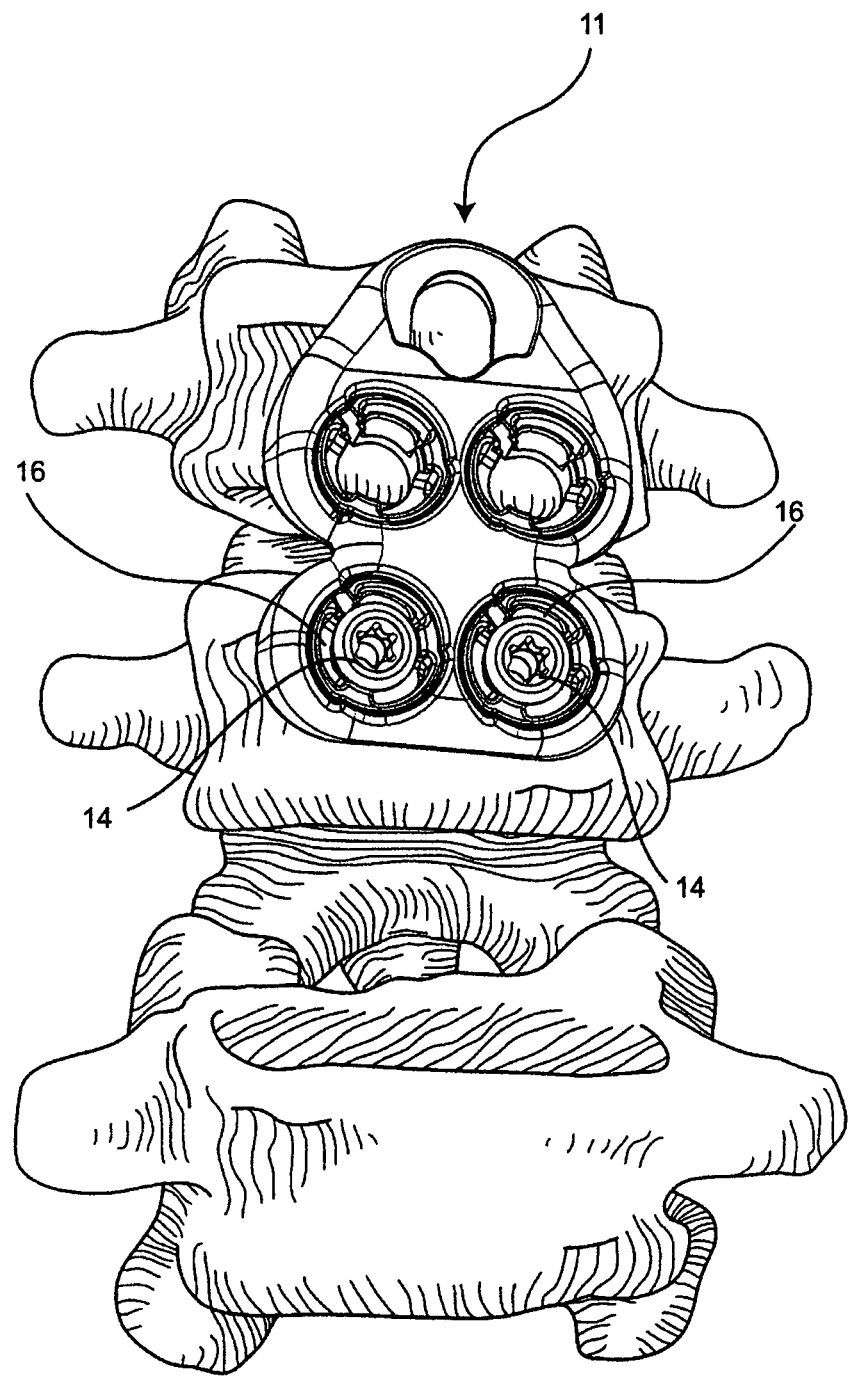
FIG. 16 is a perspective view of the lumbar plate assembly of FIG. 15, with a second fixation member affixed therethrough and one stabilization pin removed therefrom.

FIG. 16 shows the plate assembly 11 with two fixation members 14 in place. In preparation for driving the second fixation member 14, the locking guide 150 is fitted to the polyaxial locking ring 16 immediately adjacent to the already driven fixation member 14. Once fitted to the polyaxial locking ring 16, the locking guide 150 is pivoted polyaxially until the correct orientation for the second fixation member 14 is found, and the locking guide 150 is locked by lowering the lever 152. In a manner identical to that previously described for the first fixation member 14, the awl 180, depth gauge 190, tap 200 and screwdriver 210 are used to drive the second fixation member 14.

Figure 17:
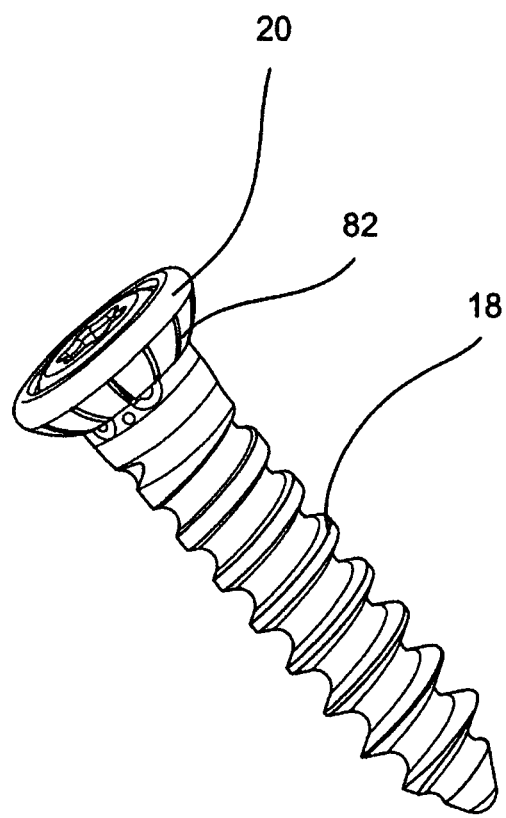
FIG. 17 is a perspective view of the compression screw and compression insert of FIG. 1.

FIG. 17 shows the compression screw 18 and the compression insert 20. In this embodiment of the invention, the compression insert 20 is a separate entity which is shaped to fit around the head of a compression screw 18. The compression insert 20 is ring-shaped and has a slanted base 82. Slits 83 may be formed in the slanted base 82. The compression insert 20 fits around the head of the compression screw 18, so that the combination of the compression insert 20/compression screw 18 are engageable with the compression aperture 36. The slanted base 82 may be conical or spherical or any other suitable shape that would allow it to smoothly slide down the ramp 42 of the compression aperture 36. The compression screw 18 may be the same screw as a fixation member 14, or may be a different screw.

Figure 18:
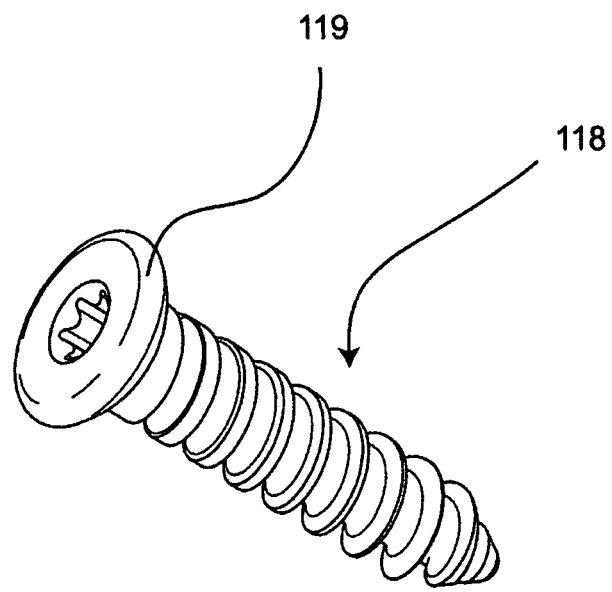
FIG. 18 is a perspective view of an alternative embodiment of a compression screw.

FIG. 18 shows an alternative compression screw 118. The compression screw 118 is a single entity and a wider head with a slanted base 119 which is engageable with the compression aperture 36 without the addition of a separate insert.

Figure 19:
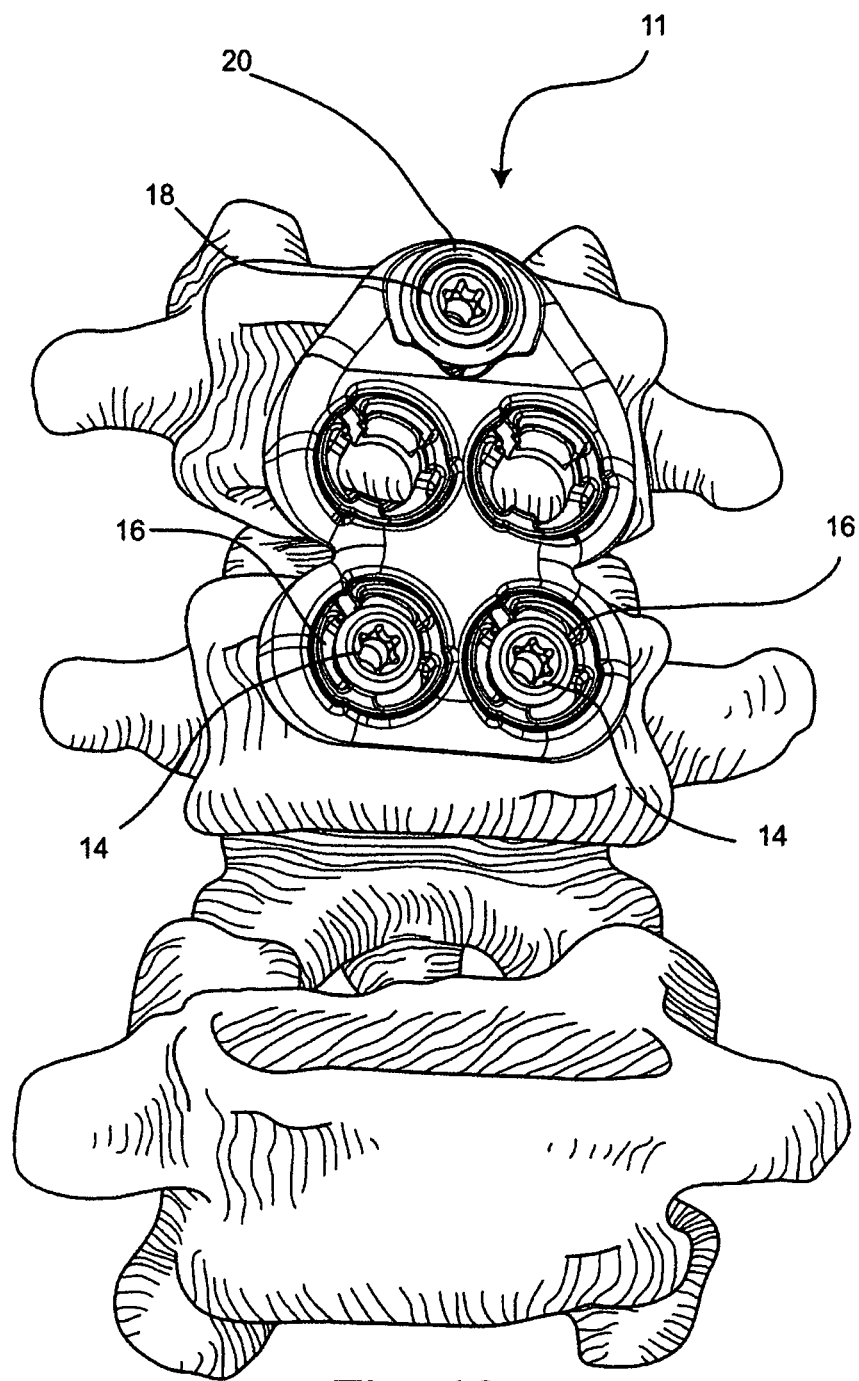
FIG. 19 is a perspective view of the lumbar plate assembly of FIG. 16, with a compression screw and compression insert.

FIG. 19 shows the plate assembly 11 with two fixation members 14, the compression insert 20 and the compression screw 18. The compression screw 18 is inserted through the compression insert 20 and tightened with the screwdriver 210. Prior to driving the compression screw 18, the locking guide 150 is attached to one of the polyaxial locking rings 16 adjacent to the compression aperture 36. As the compression screw 18 is driven, the shaft of the screwdriver 210 is visually aligned with the shaft 154 of the locking guide 150 to correctly position the angle of the compression screw 18. If necessary to break through the hard cortical bone, the awl 180 may be used prior to the screwdriver 210.

Figure 20:
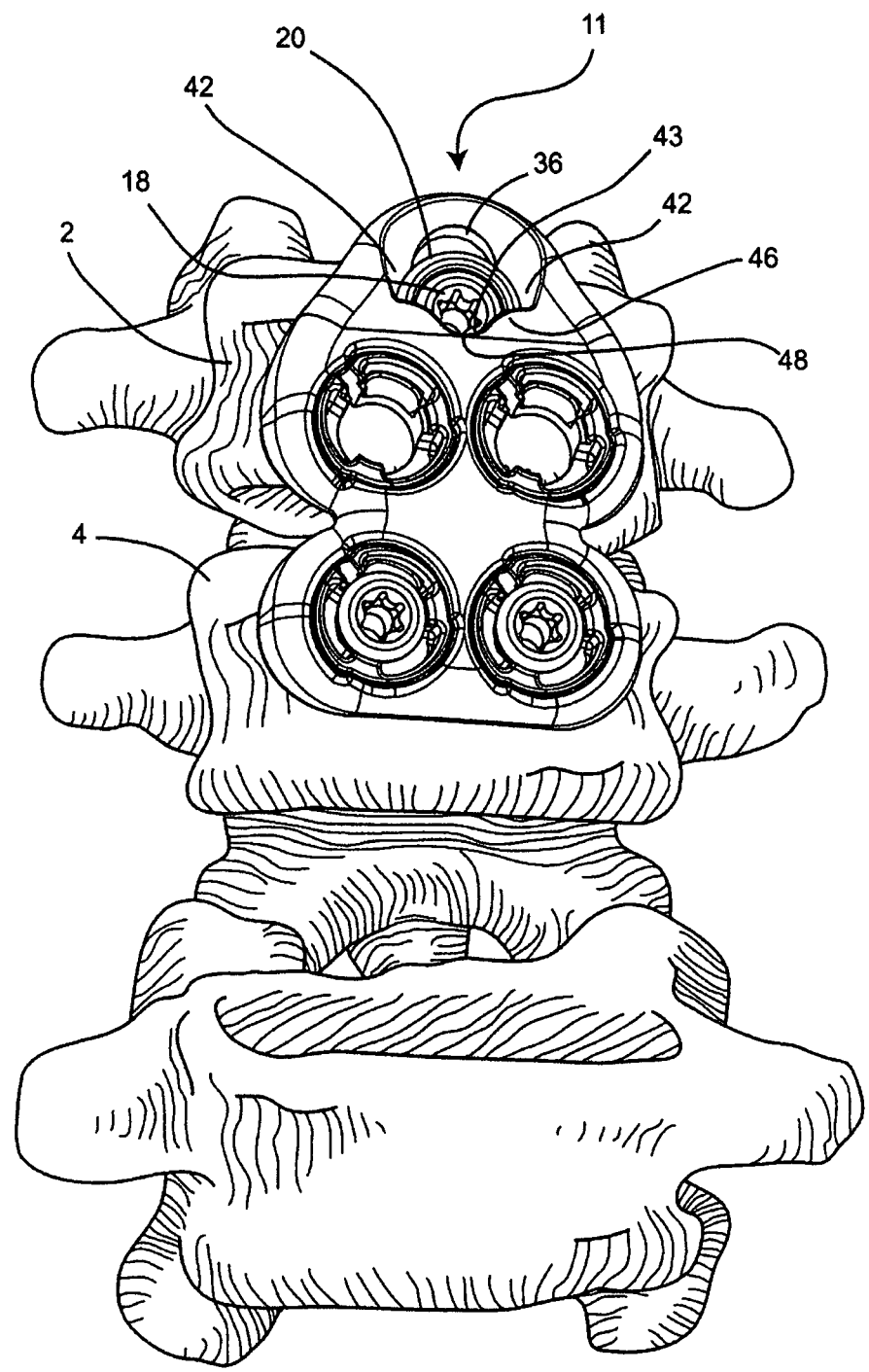
FIG. 20 is a perspective view of the lumbar plate assembly of FIG. 19, with the compression screw in a compressed state.

FIG. 20 shows the plate assembly 11 with two fixation members 14, the compression insert 20 and the compression screw 18. As the compression screw 18 is further tightened, it presses down on the compression insert 20. The slanted base 82 of the insert 20 slides down the ramps 42 of the compression aperture 36 and stops when the insert 20 meets the retaining wall 43. As the compression screw 18 and insert 20 slide down, the lip 46 protrudes over the top of the screw 18, retaining the screw 18 and preventing backout. Backout of the compression screw can occur when, over time, movement of the compression screw causes it to loosen its connections to the vertebra and the insert, and withdraw from the vertebra and the insert. The notch 48 in the lip 46 allows access for the screwdriver 210. As the compression screw 18 is tightened, the vertebrae 2, 4 are compressed together, and are shown closer together than as in FIG. 19.

Figure 21:
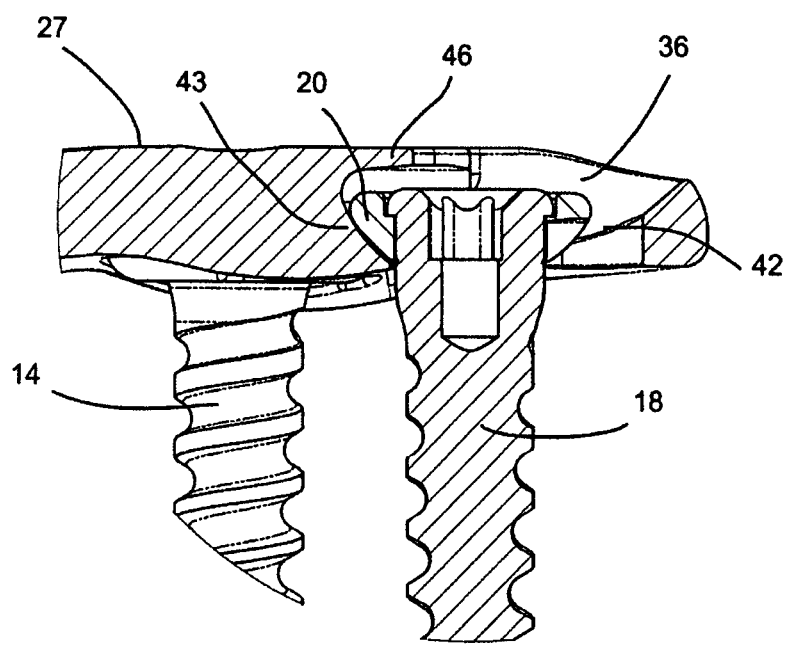
FIG. 21 is an enlarged side cross-section of a portion of the plate assembly of FIG. 20, showing how the compression screw and compression insert fit into the compression aperture.

FIG. 21 is an enlarged cross-section of a portion of a plate assembly 11 with a compressed compression screw 18, showing how the compression screw 18 and insert 20 fit into the compression aperture 36. As the compression screw 18 and insert 20 are driven in, the compression insert 20 slides down the ramps 42 of the aperture 36, until it contacts the retaining wall 43. The head of the compression screw 18 is below the surface of the outer facing side 27 of the plate 12, and the lip 46 extends over the compression screw 18, preventing backout of the compression screw 18.

Figure 22:
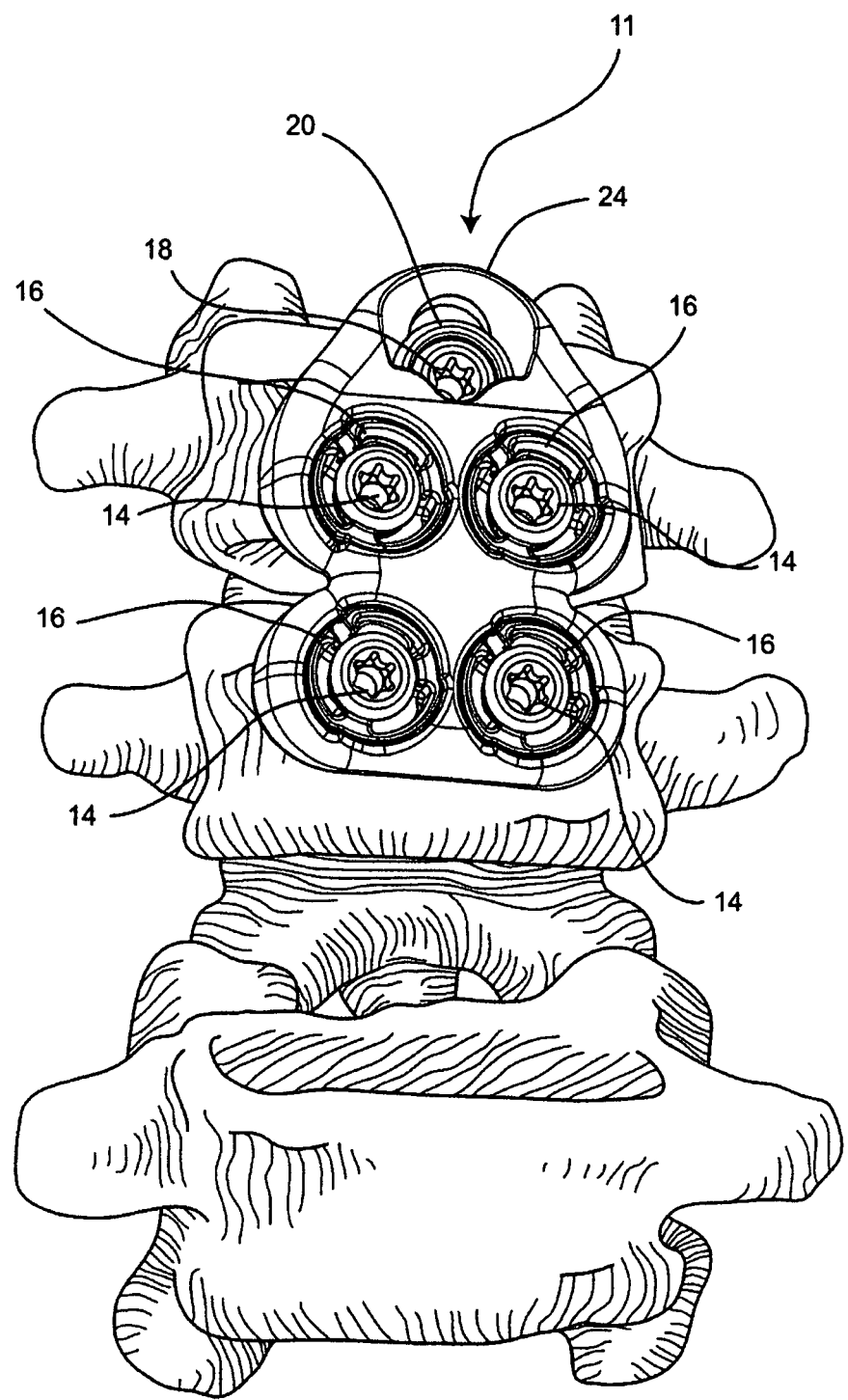
FIG. 22 is a perspective view of the lumbar plate assembly of FIG. 20, with third and fourth fixation members affixed therethrough.

Referring to FIG. 22, the plate assembly 11 with the compressed compression screw 18 and insert 20, and four fixation members 14 is shown. After compression and retention of the compression screw 18, the third fixation member 14 is placed and driven in, with the same locking guide and tools and in the manner described above as for the first and second fixation members 14. The third fixation member 14 is placed in one of the paired polyaxial locking rings 16/fixation member holes 28 in the first end 24, adjacent to the compression screw 18. The fourth fixation member 14 is driven into the remaining empty polyaxial locking ring 16/fixation member hole 28 pair on the first end 24, adjacent to the compression screw 18.

Figure 23:
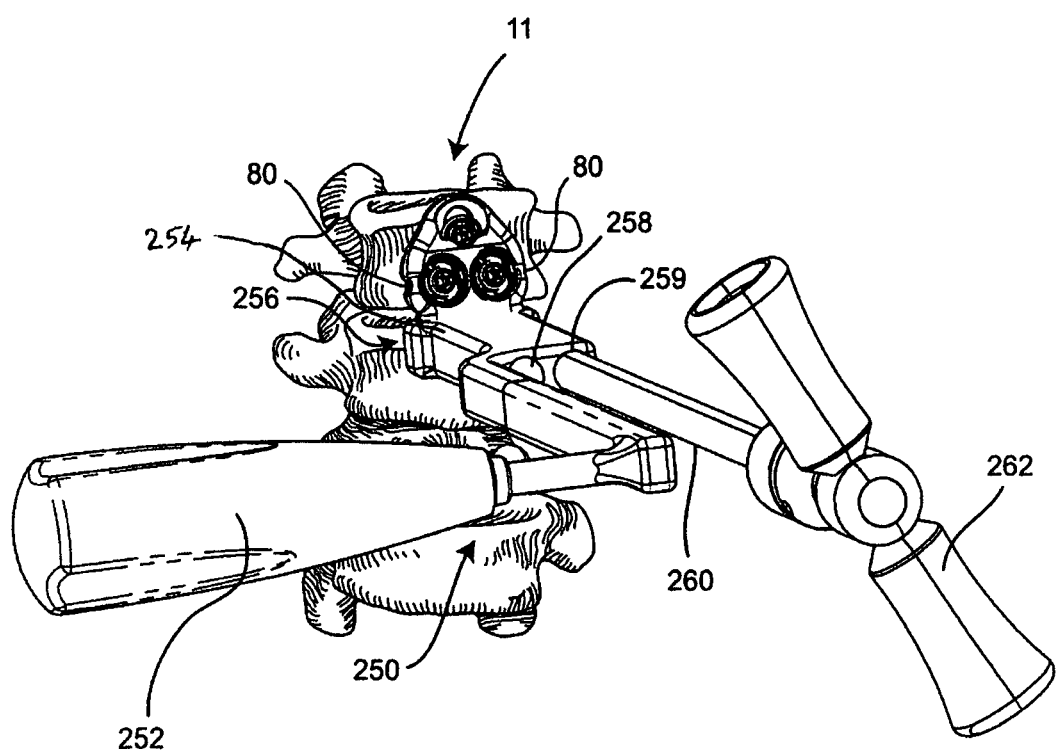
FIG. 23 is a perspective view of the lumbar plate assembly of FIG. 21, with a anti-torque key and a torque wrench.

Referring to FIG. 23, an anti-torque key 250 and an articulating torque wrench 260 are shown connected to the plate assembly 11 of FIG. 22. The anti-torque key 250 is a double-barreled torque limiting device which releasably engages the plate assembly 11 and stabilizes the assembly 11 while the polyaxial locking rings 16 are torqued. The anti-torque key 250 has a handle 252, a double-barreled shaft 254, and a plate connector 256. Two tool bores 258, 259 extend through the length of the shaft 254. The plate connector 256 is shaped to releasably fit into two notches 80 on the plate assembly 11. One pair of notches 80 are located on the first end 24, one adjacent to each fixation member hole 28. Two additional notches 80 are located on the second end 25, one adjacent to each fixation member hole 28. When the plate connector 256 is fit into one pair of notches 80, the tool bores 258, 259 are aligned directly over the two adjacent polyaxial locking rings 16.

The articulating torque wrench 260 is shown inserted in the tool bore 259 of the anti-torque key 250. The wrench 260 has a handle 262, a shaft 264 and a double universal joint connection 266.

Figure 24:
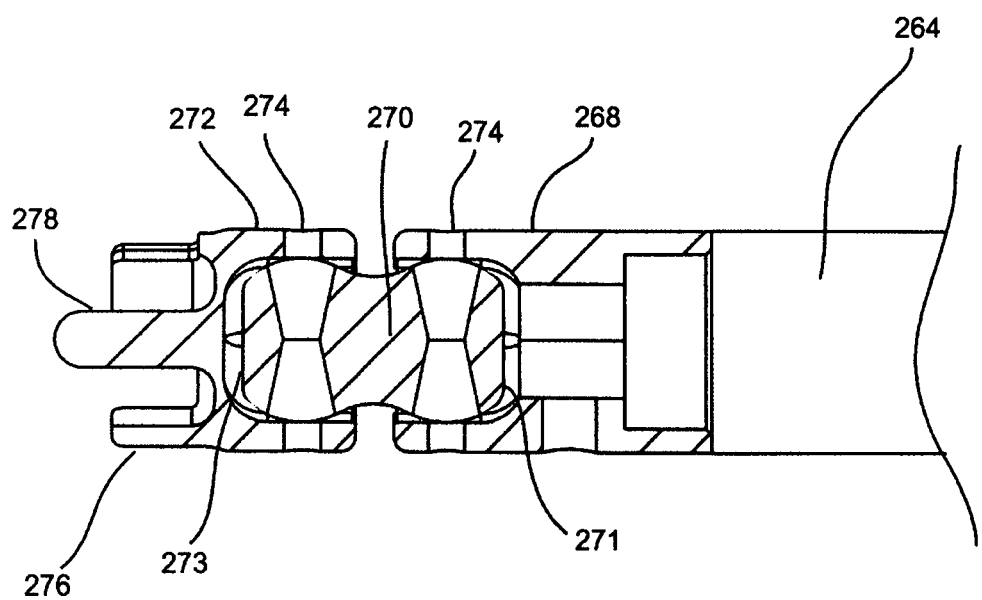
FIG. 24 is an enlarged cutaway view of a double universal joint connection of the torque wrench of FIG. 23.

FIG. 24 shows an enlarged cutaway view of the distal end of the articulating torque wrench 260. The shaft 264 terminates at the double universal joint connection 266, which comprises a first socket 268, a twin ball connector 270 and a second socket 272. The twin ball connector 270 is peanut-shaped, with a first hex ball 271 at one end and a second hex ball 273 at the opposite end.

The first socket 268 extends distally from the shaft 264, and the first hex ball 271 pivotably fits inside the first socket 268, forming a universal joint. A pin 274 retains the first hex ball 271 in the first socket 268 while still allowing the first hex ball 271 to pivot within the socket 268. The second hex ball 273 pivotably fits inside the second socket 272, forming a second universal joint. A second pin 274 retains the second hex ball 273 in the second socket 272 while still allowing the second hex ball 273 to pivot within the socket 272. The hexagonal configuration of the first and second hex balls 271, 273 prevent them from rotating within the first and second sockets 268, 272 when the wrench 260 is turned.

Three prongs 276 on the distal end of the second socket 268 are shaped to fit in the pockets 64 of the polyaxial locking ring 16. A rounded finger 278 is shaped to fit in the torx slot 144 of the fixation member 14, but its rounded shape prevents it from engaging with the torx slot 144 and turning the fixation member 14.

The articulating torque wrench 260 is used to torque all four polyaxial locking rings to 12 newton-meters. The wrench 260 is slid into one of the tool bores 258, 259 of the anti-torque key 250, until the prongs 276 on the double universal joint connection 266 engage in the pockets 64 of the polyaxial locking ring 16. The pivotability of the double universal joint connection 266 allows the wrench 260 to engage with the polyaxial locking ring 16 at whatever orientation the polyaxial locking ring 16 and fixation member 14 are. The wrench 260 is turned, simultaneously turning the polyaxial locking ring 16. The engagement of the plate connector 256 with the notches 80 prevent the plate assembly 11 from shifting as the ring 16 is torqued.

As the polyaxial locking ring 16 turns, the projections 60 on the outer ring wall 54 are forced past the indentations 32 in the fixation member hole wall 30. The inner diameter of the polyaxial locking ring 16 decreases and grips the head of the fixation member 14. Once the polyaxial locking ring 16 is thus torqued, residual compression and the outward spring bias of the polyaxial locking ring 16 keep it locked in orientation relative to the plate 12, and locked around the head of the fixation member 14. In addition, locking of the polyaxial locking ring 16 to the fixation member 14 prevents backout of the fixation member 14. Backout of the fixation member can occur when, over time, movement of the fixation member causes it to loosen its connections to the vertebra and the plate, and withdraw from the vertebra and the plate.

Once one pair of polyaxial locking rings 16 are torqued, the anti-torque key 250 is moved to the other end 24, of the plate assembly 11, and the remaining two polyaxial locking rings 16 are torqued in the same manner as described previously.

In an alternative embodiment of the invention, a plurality of fixed orientation locking rings (not shown) can be implemented instead of polyaxial locking rings 16. Each fixed orientation locking ring receives a fixation member 14 in a fixed orientation, preventing polyaxial pivoting of the fixation member 14 prior to driving the fixation member 14 into the vertebra. Torqueing the fixed orientation locking ring with the fixation member 14 within locks the fixed orientation locking ring to the plate 12, and locks the fixed orientation locking ring around the head of the fixation member 14, in the same manner as described above for a polyaxial locking ring 16/fixation member 14 combination.

Figure 25:
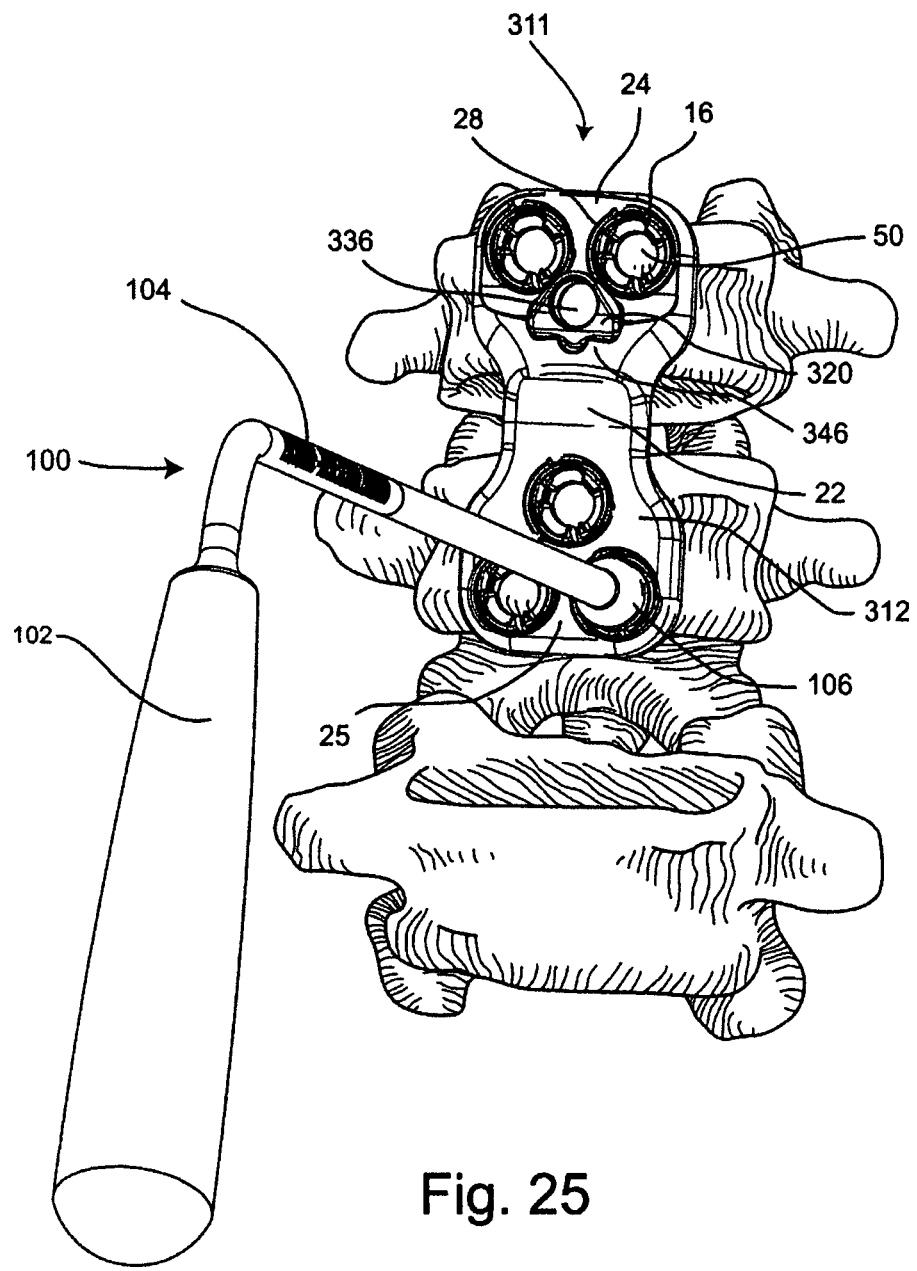
FIG. 25 is a perspective view of an alternative lumbar plate assembly and a plate holder, held against a portion of the spine.

Referring to FIG. 25, an alternative embodiment of a lumbar plate assembly 311 is shown, held against a portion of the spine by a plate holder 100. The lumbar plate assembly 311 comprises a lumbar plate 312, a compression insert 320 and a plurality of polyaxial locking rings 16. The lumbar plate 312 has a first end 24 and a second end 25, and a shank 22 which extends between the two ends 24, 25. The lumbar plate 312 has five fixation screw holes 28 and one compression aperture 336, which is shaped to guide and retain the compression insert 320 and a compression screw 18. Although five fixation screw holes 28 and associated polyaxial locking rings 16 are shown in this embodiment, other embodiments may include more or fewer fixation screw holes 28 and polyaxial locking rings 16.

In this embodiment of the invention, the compression insert 320 is an integral part of the lumbar plate assembly 311 and cannot be removed from the lumbar plate assembly 311. The compression insert 320 is shaped to receive a compression screw 18, and when the compression screw 18 is driven into the vertebra in the manner previously described for the compression screw 18/compression insert 20 combination, the compression insert 320 is guided by the compression aperture 336. A lip 346 which is a monolithic part of the plate 312 prevents backout of the compression screw 18 and insert 320.

The plate holder 100 is configured to engage with any polyaxial locking ring 16 on the plate assembly 311, and allows the plate to be moved about, held in place and stabilized prior to and during fixation to the vertebrae. Similarly, the plate holder 100 can engage with any polyaxial locking ring on the plate assembly 11 and therefore be used in conjunction with the plate assembly 11, or any other plate assembly with polyaxial locking rings 16. The plate holder 100 has a handle 102, a shaft 104, and a holding mechanism 106.

Figure 26:
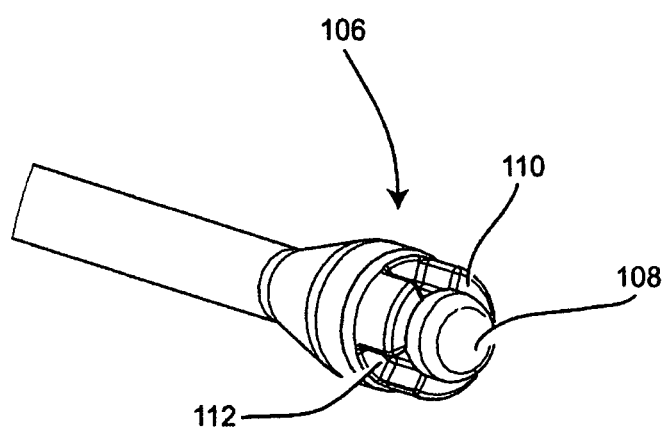
FIG. 26 is an enlarged perspective view of a holding mechanism of the plate holder of FIG. 25.

FIG. 26 displays the holding mechanism 106 in greater detail. The holding mechanism 106 is designed to fit into any polyaxial locking ring 16. The holding mechanism 106 has an outwardly projecting knob 108 which is subtended by three spokes 110 alternating with three notches 112. The knob 108 is shaped to fit in the bore 50 of the polyaxial locking ring 16. The spokes 110 fit into the pockets 64, and the ribs 66 and split rib 68 of the ring 16 fit into the notches 112 of the mechanism 106. The handle of the plate holder 100 is twisted, and the holding mechanism 106 with the now attached polyaxial locking ring 16 twist within the fixation screw hole 28. The projections 60 on the outer ring wall 54 of the polyaxial locking ring 16 are forced past the indentations 32 in the fixation member hole wall 30. The inner diameter of the polyaxial locking ring 16 decreases and grips the knob 108 and the spokes 110. The holding mechanism can be fitted into the locking ring 16 at any one of three orientations, because any spoke 110 can fit into any pocket 64 on the locking ring 16. This allows flexibility in holding and positioning the plate assembly 311 or 11 prior to fixation.

Figure 27:
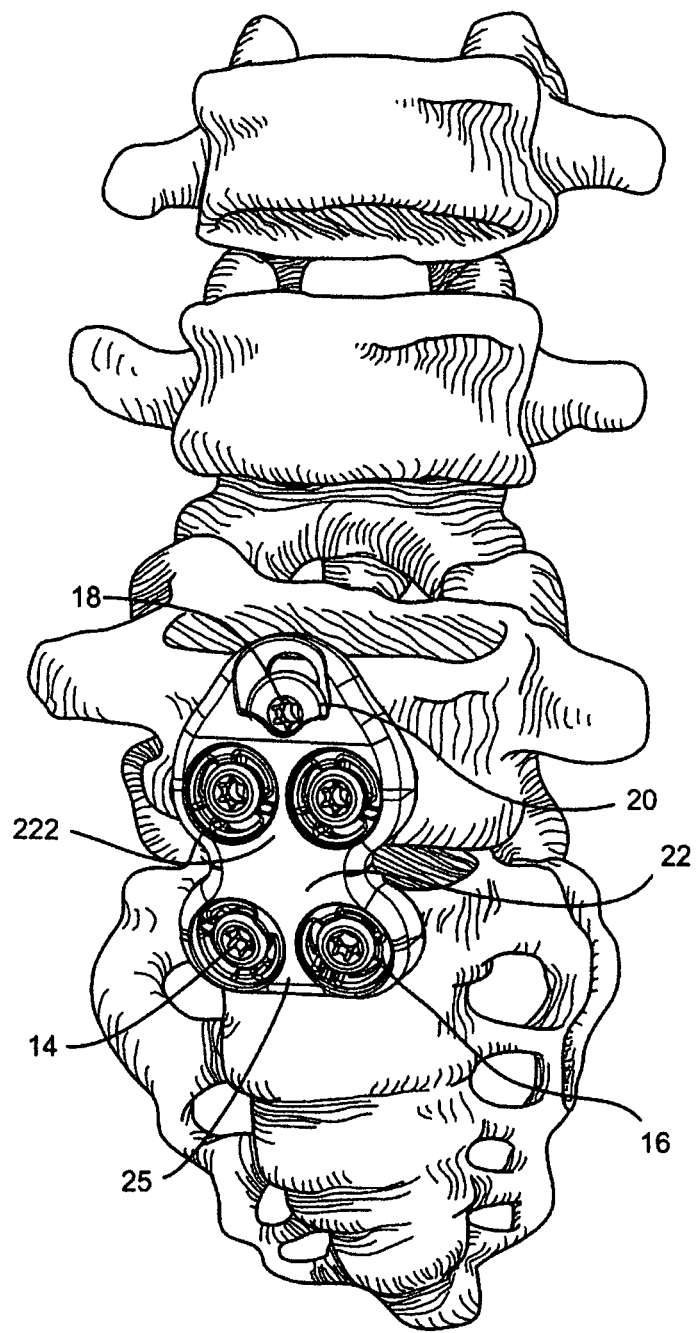
FIG. 27 is a perspective view of a sacral plate assembly affixed anteriorly to a portion of the spine.

Referring to FIG. 27, a sacral plate 222 with associated polyaxial locking rings 16, fixation members 14, compression screw 18 and compression insert 20 is shown. The shank 22 of the sacral plate 222 is bent to fit the angle between the sacrum and the L5 vertebra. In this embodiment, five fixation members 14 are employed, including a third fixation member 14 on the second end 25.

Figure 28:
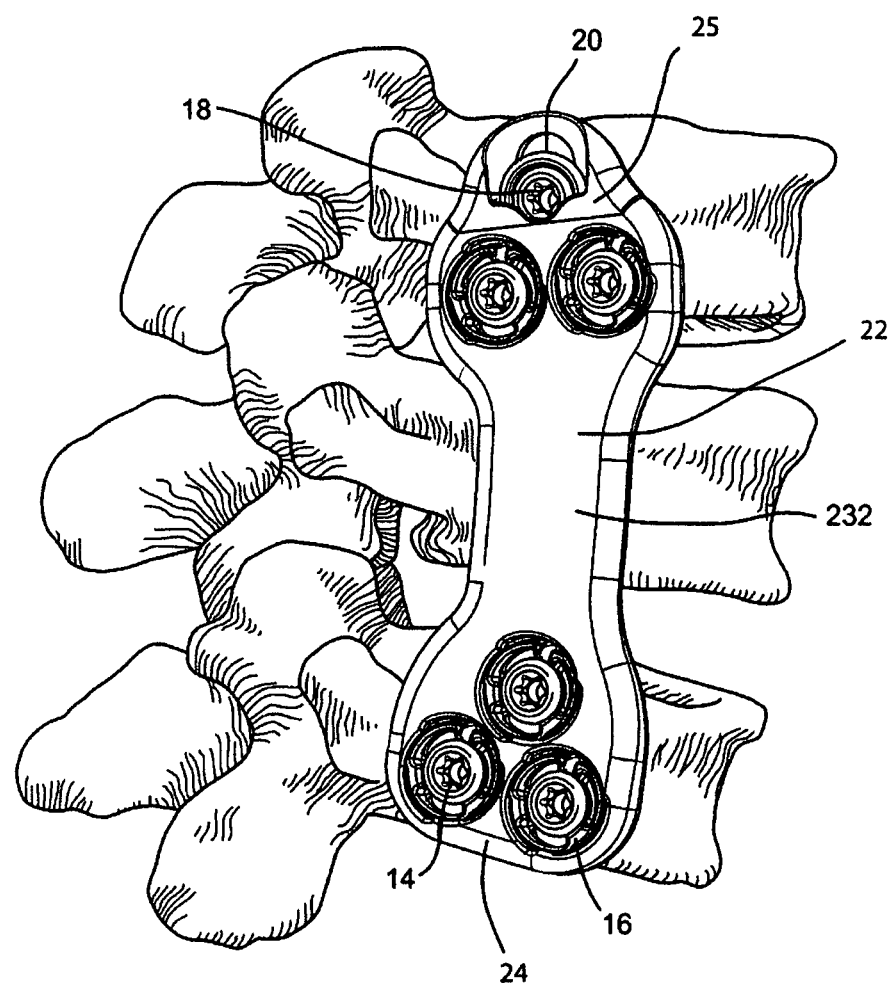
FIG. 28 is a perspective view of a thoracolumbar plate assembly affixed laterally to a portion of the spine.

Referring to FIG. 28, a thoracolumbar plate 232 with associated polyaxial locking rings 16, fixation members 14, a compression screw 18 and a compression insert 20 is shown. The thoracolumbar plate 232 has an elongated shank 22 that extends between the first end 24 and the second end 25, so that the plate can span across three vertebrae. The thoracolumbar plate 232 is configured to be secured laterally to the vertebrae, instead of anteriorly. The shank 22 of the thoracolumbar plate 232 is curved to follow the lordotic curve of the spine.

Figure 29:
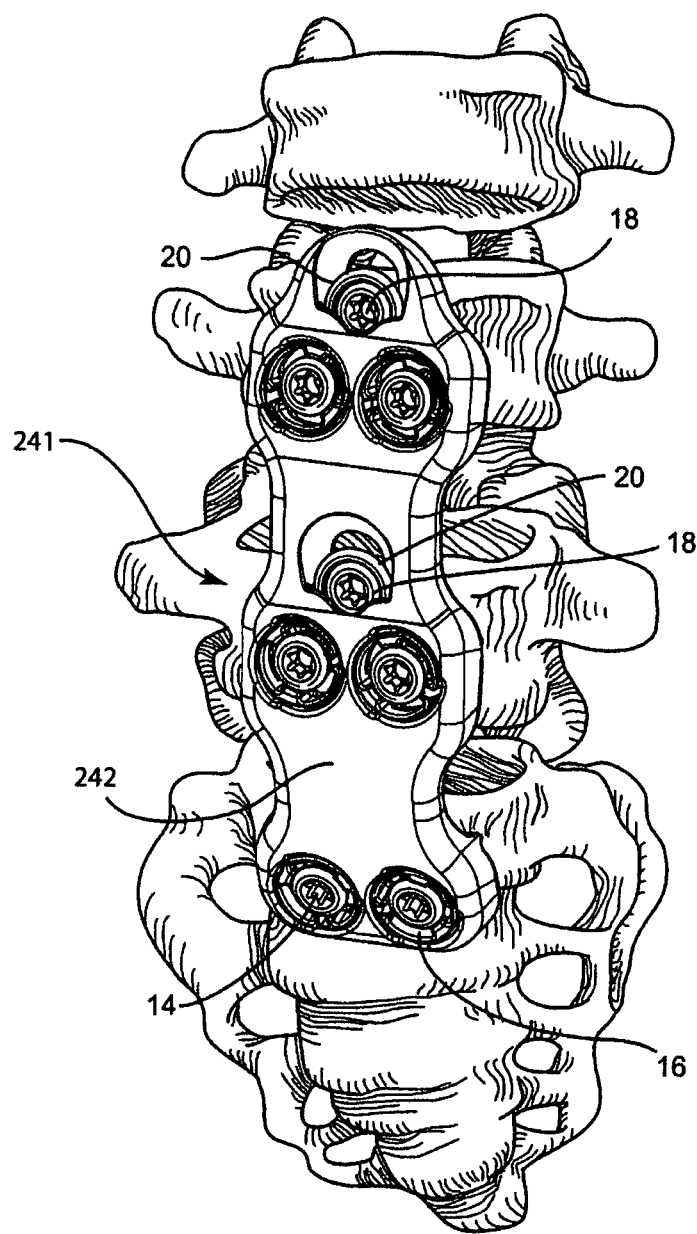
FIG. 29 is a perspective view of a two level sacral plate assembly affixed anteriorly to a portion of the spine.

Referring to FIG. 29, a two-level sacral plate assembly 241 with two compression screws 18 and two compression inserts 20 is shown. The assembly 241 comprises a two-level sacral plate 242 and polyaxial locking rings 16. The two-level sacral plate 242 has an elongated shank 22 so that it can span from the sacrum to the L4 vertebra. Each compression screw 18/compression insert 20 pair provides compression to one vertebral level, so compression is accomplished at two adjacent levels.

The present invention may be embodied in other specific forms without departing from its spirit or essential characteristics. It is appreciated that various features of the above-described examples can be mixed and matched to form a variety of other alternatives, each of which may have different plates, compression components or fixation members according to the invention. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A spinal compression implant comprising:
   a plate attachable to a first vertebra, the plate having an outer side and a bone apposition side;
   a slot formed in the plate, the slot having a generally oval, elongated shape defining first and second ends and lateral sides, the slot further including a ramp disposed at the first end and extending along the lateral sides;
   a lip monolithically formed as a part of the plate, the lip being disposed at the second end of the slot and extending over a portion of the ramp; and
   a screw having threads, the screw insertable in the slot and threadable in a second vertebra, the screw having a screw head with an upper surface apart from the threads, wherein tightening of the screw moves the screw head along the ramp such that at least a portion of the upper surface of the screw head is positioned under the lip to inhibit backout of the screw.

2. The spinal compression implant of claim 1, further comprising:
   at least one fixation hole formed in the plate;
   a fixation screw insertable in the at least one fixation hole and threadable in the first vertebra to attach the plate to the first vertebra.

3. The spinal compression implant of claim 2, further comprising:
   at least one polyaxial ring pivotable in the at least one fixation hole to orient the fixation screw with respect to the first vertebra, the at least one polyaxial ring having an outer surface with at least one projection that fits into a matching indentation formed in the at least one fixation hole.

4. The spinal compression implant of claim 3, wherein the at least one polyaxial ring has a trilobial shape, the at least one projection includes three projections, and the matching indentation has three indentations.

5. The spinal compression implant of claim 3, wherein the at least one polyaxial ring locks the fixation screw and thereby fixes the orientation of the fixation screw with respect to the plate.

6. The spinal compression implant of claim 3, wherein the at least one polyaxial ring prevents withdrawal of the fixation screw from the plate.

7. The spinal compression implant of claim 2, further comprising:
   at least one second hole formed in the plate; and
   a second screw insertable in the at least one second hole and threadable in the second vertebra.

8. The spinal compression implant of claim 2, wherein the plate has a first segment and a second segment, the first segment having the slot and a first of the at least one fixation hole located thereon and the second segment having a second of the at least one fixation hole located thereon.

9. The spinal compression implant of claim 8, wherein the first segment and the second segment are connected by a bridge region.

10. The spinal compression implant of claim 9, wherein a region of the first segment where the slot is located is narrower in width than another region of the first segment.

11. The spinal compression implant of claim 2, wherein at least one of the fixation screw and the screw having threads has a cancellous thread near a head of the respective screw and the cancellous thread transitions to a cortical thread near a tip of the respective screw.

12. The spinal compression implant of claim 1, wherein the bone apposition side has a longitudinal axis and a transverse axis, and the plate is bent about the transverse axis and curved about the longitudinal axis.

13. The spinal compression implant of claim 1, wherein the plate has at least one elongated ridge extending normal to the bone apposition side.

14. The spinal compression implant of claim 1, further comprising:
   a compression insert configured to receive the screw, the compression insert being non-removeably attached to the plate.

15. A spinal compression implant comprising:
   a plate attachable to a first vertebra, the plate having an outer side and a bone apposition side;
   a slot formed in the plate, the slot having a generally oval, elongated shape and a ramp;
   a lip monolithically formed as a part of the plate, the lip extending over a portion of the ramp; and
   a screw having threads, the screw insertable in the slot and threadable in a second vertebra, the screw having a screw head with an upper surface apart from the threads, wherein tightening of the screw moves the screw head along the ramp such that at least a portion of the upper surface of the screw head is positioned under the lip to inhibit backout of the screw,
   wherein the ramp of the slot includes first and second portions that each extend from the outer side of the plate toward the bone apposition side of the plate, wherein when viewed along an axis passing through the slot, the first portion extends in a clockwise direction about the axis and the second portion extends in a counter-clockwise direction about the axis.

16. The spinal compression implant of claim 15, further comprising:
   at least one fixation hole formed in the plate;
   a fixation screw insertable in the at least one fixation hole and threadable in the first vertebra to attach the plate to the first vertebra.

17. The spinal compression implant of claim 16, further comprising:
   at least one polyaxial ring pivotable in the at least one fixation hole to orient the fixation screw with respect to the first vertebra, the at least one polyaxial ring having an outer surface with at least one projection that fits into a matching indentation formed in the at least one fixation hole.

18. The spinal compression implant of claim 17, wherein the at least one polyaxial ring has a trilobial shape, the at least one projection includes three projections, and the matching indentation has three indentations.

19. The spinal compression implant of claim 17, wherein the at least one polyaxial ring locks the fixation screw and thereby fixes the orientation of the fixation screw with respect to the plate.

20. The spinal compression implant of claim 16, wherein the plate has a first segment and a second segment, the first segment having the slot and a first of the at least one fixation hole located thereon and the second segment having a second of the at least one fixation hole located thereon, wherein the first segment and the second segment are connected by a bridge region, and wherein a region of the first segment where the slot is located is narrower in width than another region of the first segment.

21. The spinal compression implant of claim 15, wherein the bone apposition side has a longitudinal axis and a transverse axis, and the plate is bent about the transverse axis and curved about the longitudinal axis.

22. The spinal compression implant of claim 15, wherein the plate has at least one elongated ridge extending normal to the bone apposition side.

23. The spinal compression implant of claim 15, further comprising:
    a compression insert configured to receive the screw, the compression insert being non-removeably attached to the plate.

\* \* \* \* \*